(12) United States Patent
Harris et al.

(10) Patent No.: US 10,350,050 B2
(45) Date of Patent: Jul. 16, 2019

(54) METHOD FOR GASTRIC VOLUME REDUCTION SURGERY

(75) Inventors: Jason L. Harris, Mason, OH (US);
Mark S. Zeiner, Mason, OH (US);
Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1918 days.

(21) Appl. No.: 12/113,784

(22) Filed: May 1, 2008

(65) Prior Publication Data

US 2009/0276055 A1    Nov. 5, 2009

(51) Int. Cl.
| | |
|---|---|
| *A61F 2/04* | (2013.01) |
| *A61F 2/07* | (2013.01) |
| *A61M 29/00* | (2006.01) |
| *A61B 17/04* | (2006.01) |
| *A61B 17/11* | (2006.01) |
| *A61F 5/00* | (2006.01) |
| *A61B 17/00* | (2006.01) |
| *A61B 17/06* | (2006.01) |
| *A61M 25/00* | (2006.01) |

(52) U.S. Cl.
CPC ............ *A61F 2/04* (2013.01); *A61B 17/0401* (2013.01); *A61B 17/0482* (2013.01); *A61B 17/1114* (2013.01); *A61F 5/0076* (2013.01); *A61B 17/0467* (2013.01); *A61B 17/0469* (2013.01); *A61B 17/0487* (2013.01); *A61B 2017/00818* (2013.01); *A61B 2017/0409* (2013.01); *A61B 2017/0414* (2013.01); *A61B 2017/0417* (2013.01); *A61B 2017/0464* (2013.01); *A61B 2017/0475* (2013.01); *A61B 2017/06052* (2013.01); *A61B 2017/1139* (2013.01); *A61F 5/0086* (2013.01); *A61M 2025/0024* (2013.01)

(58) Field of Classification Search
CPC .... A61F 5/0076; A61F 5/0079; A61F 5/0083; A61F 5/0086; A61F 2002/045; A61F 2/848; A61F 2002/8483
USPC ..... 604/8, 28, 43; 623/23.65, 23.7; 600/123, 600/136, 139; 606/108, 139, 142, 144, 606/152, 153, 170, 185
See application file for complete search history.

(56) References Cited

U.S. PATENT DOCUMENTS

| | | | | |
|---|---|---|---|---|
| 4,315,509 | A | * | 2/1982 | Smit ............................ 606/108 |
| 4,668,225 | A | * | 5/1987 | Russo et al. .................. 604/270 |
| 5,355,897 | A | * | 10/1994 | Pietrafitta et al. ............ 128/898 |
| 5,820,584 | A | * | 10/1998 | Crabb .................... A61F 5/0079 604/264 |
| 6,558,400 | B2 | | 5/2003 | Deem et al. |
| 2004/0092892 | A1 | * | 5/2004 | Kagan et al. ................. 604/264 |
| 2004/0107004 | A1 | * | 6/2004 | Levine et al. ............. 623/23.64 |
| 2005/0075622 | A1 | * | 4/2005 | Levine et al. ................ 604/500 |

(Continued)

OTHER PUBLICATIONS

Medical Dictionary from thefreedictionary.com "chyme" accessed Tuesday, Apr. 24, 2012. http://medical-dictionary.thefreedictionary.com/chyme.*

(Continued)

*Primary Examiner* — Adam Marcetich

(57) ABSTRACT

A method for treating a patient includes creating at least one incision to gain access to an peritoneal cavity, performing a gastric volume reduction procedure and introducing a device to prevent gastric contents from interacting with at least a portion of the duodenum.

13 Claims, 42 Drawing Sheets

(56) References Cited

U.S. PATENT DOCUMENTS

| | | | |
|---|---|---|---|
| 2005/0085923 A1* | 4/2005 | Levine | A61B 17/0401 623/23.65 |
| 2005/0250980 A1* | 11/2005 | Swanstrom et al. | 600/37 |
| 2006/0020247 A1* | 1/2006 | Kagan et al. | 604/264 |
| 2006/0064120 A1* | 3/2006 | Levine | A61F 2/04 606/153 |
| 2006/0074473 A1* | 4/2006 | Gertner | A61F 5/0086 607/133 |
| 2006/0157067 A1* | 7/2006 | Saadat | A61B 17/00491 128/898 |
| 2007/0083271 A1* | 4/2007 | Levine et al. | 623/23.64 |
| 2007/0282454 A1* | 12/2007 | Krueger et al. | 623/23.65 |
| 2008/0065136 A1* | 3/2008 | Young | 606/191 |
| 2008/0147002 A1* | 6/2008 | Gertner | A61N 1/36007 604/104 |
| 2008/0208239 A1* | 8/2008 | Annunziata | 606/191 |
| 2008/0249566 A1* | 10/2008 | Harris et al. | 606/220 |
| 2008/0255587 A1* | 10/2008 | Cully | A61F 2/04 606/139 |
| 2008/0319470 A1* | 12/2008 | Viola | A61B 17/0643 606/191 |
| 2009/0264808 A1* | 10/2009 | Young | 604/8 |

OTHER PUBLICATIONS

"Chyme Definition" from medterms.com accessed Tuesday, Apr. 12, 2012. http://www.medterms.com/script/main/art.asp?articlekey=11119.*

* cited by examiner

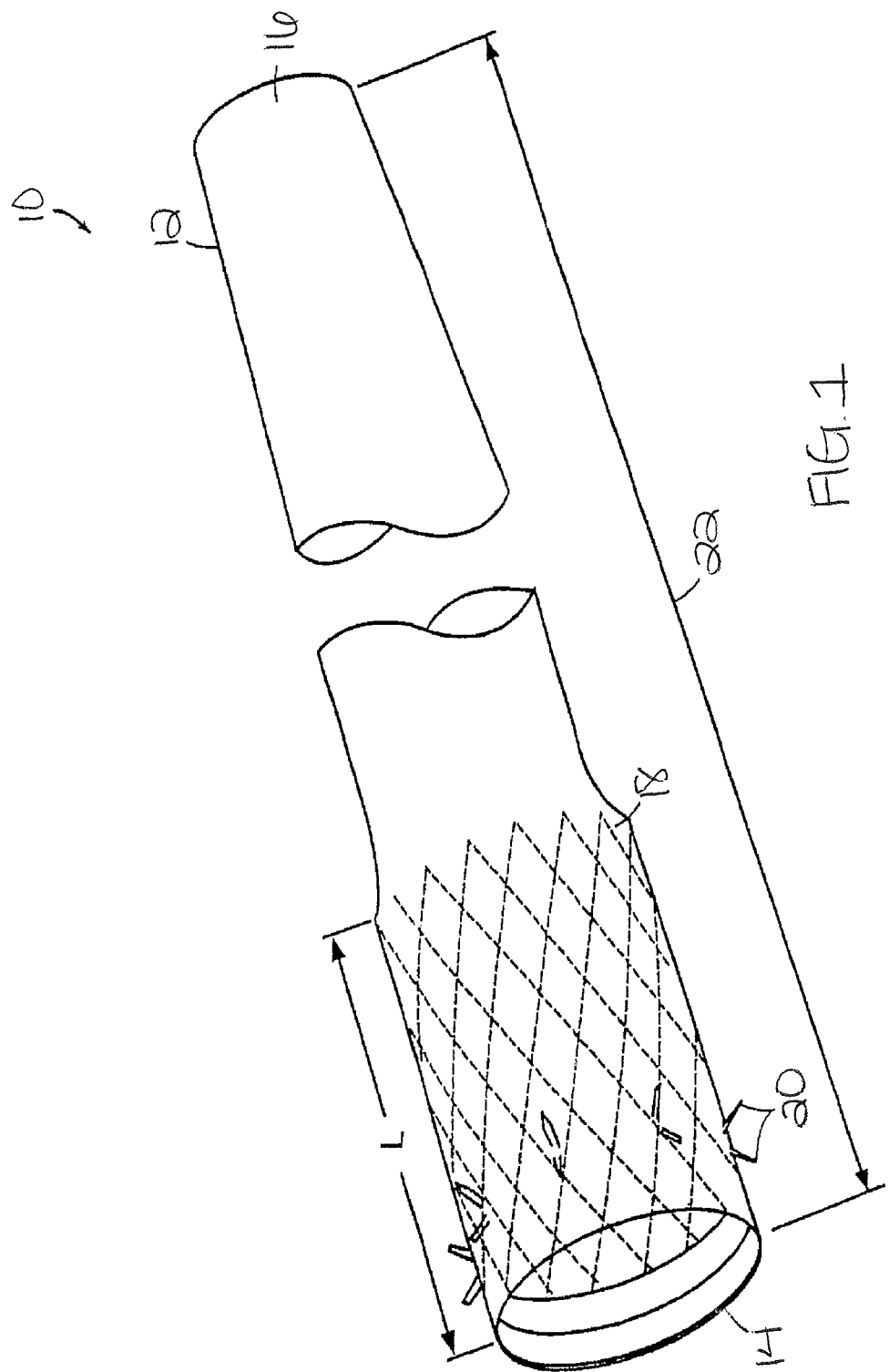

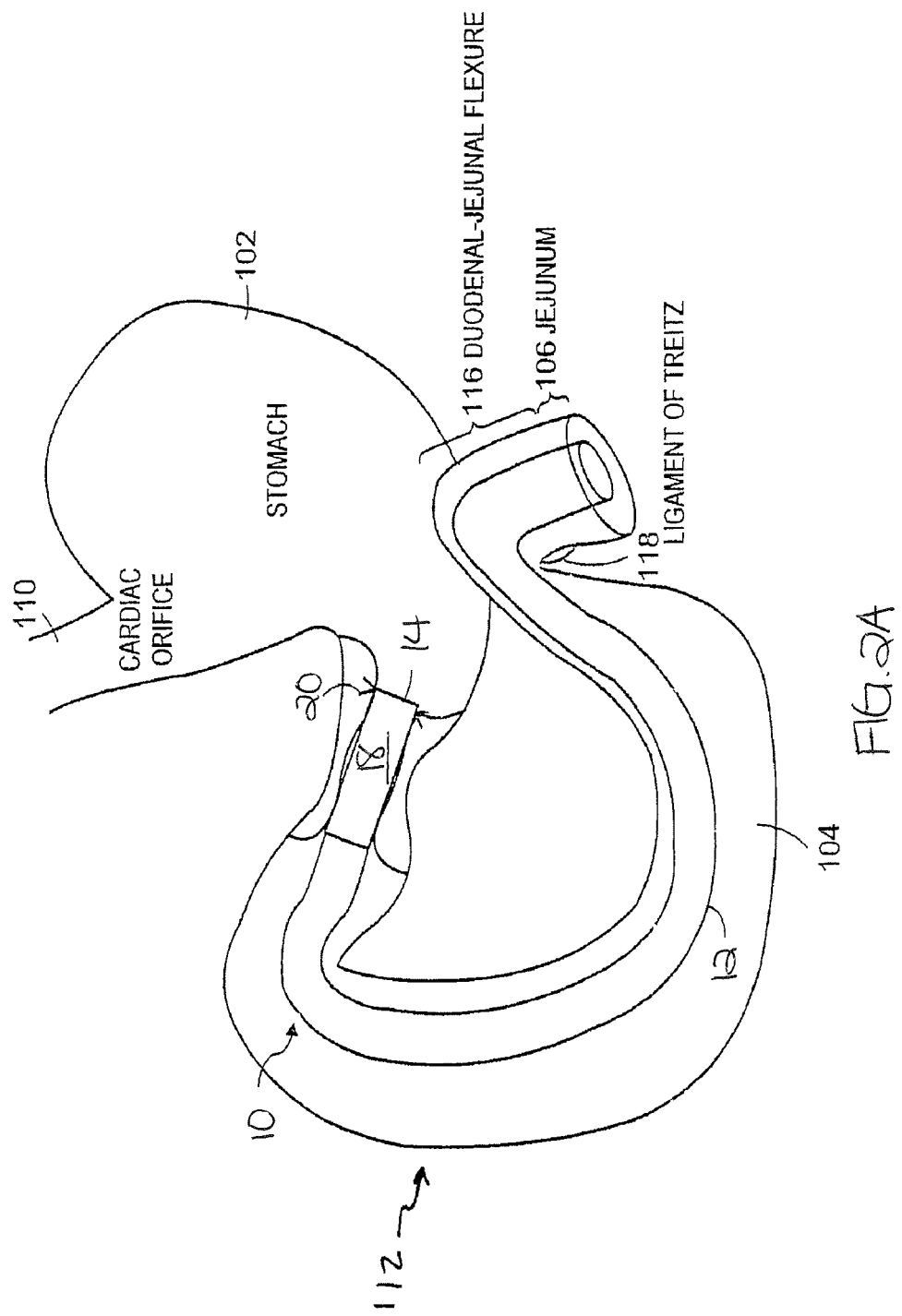

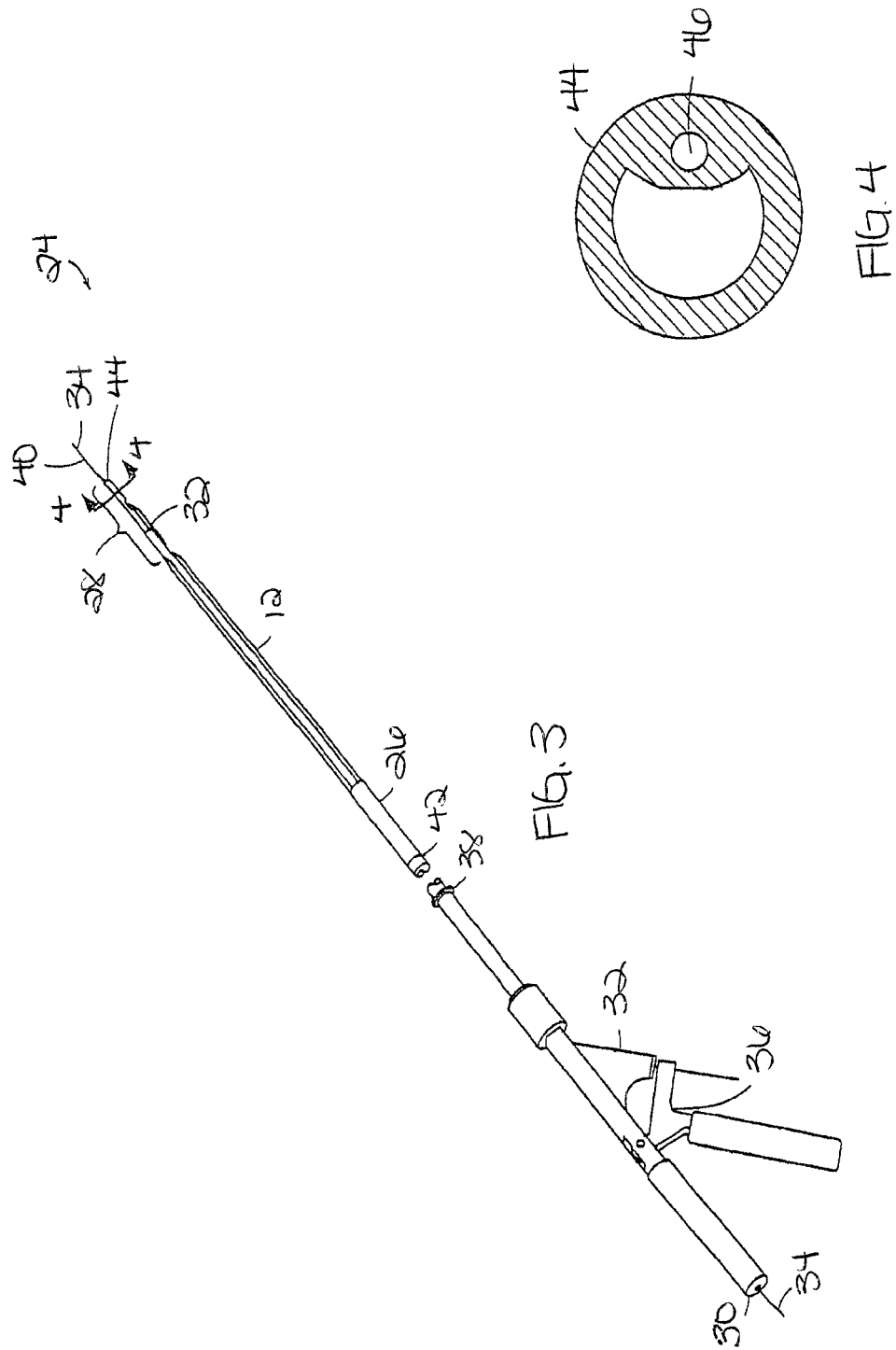

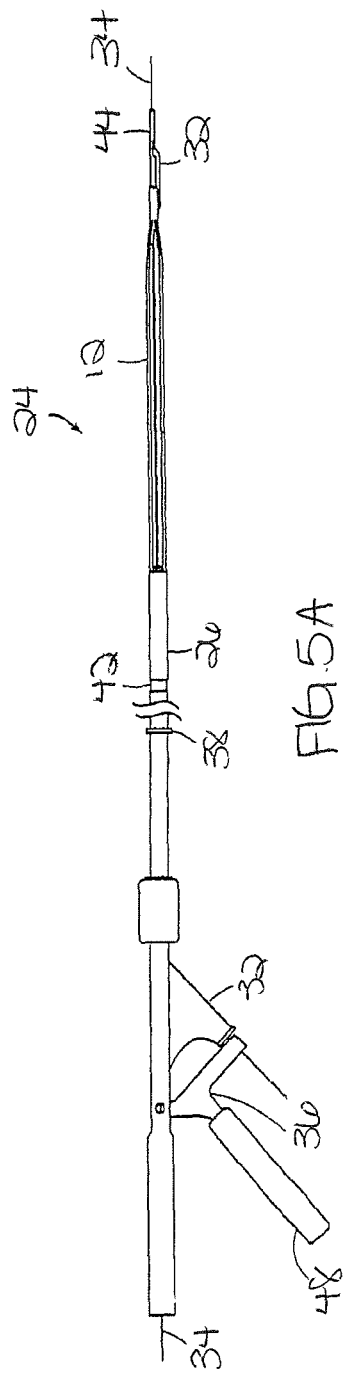

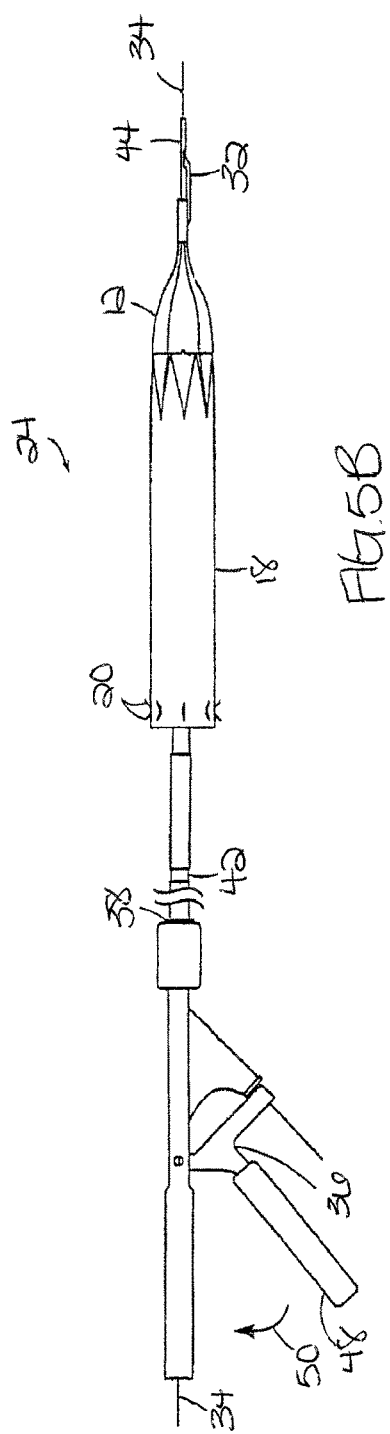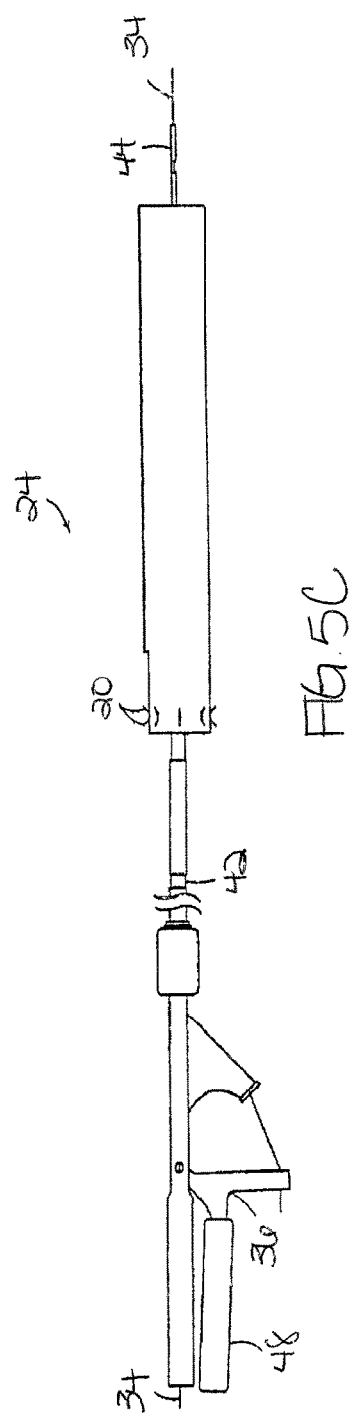

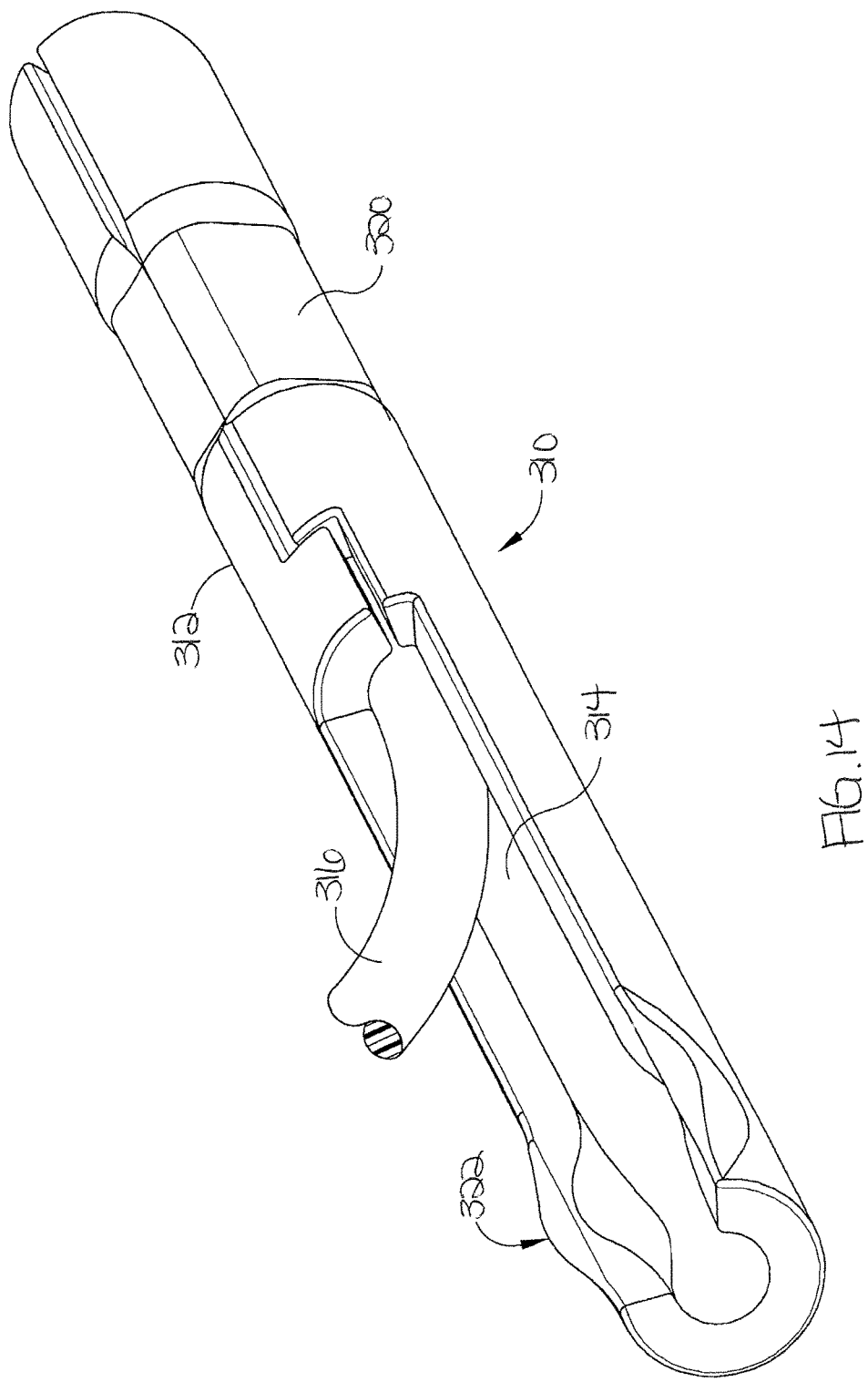

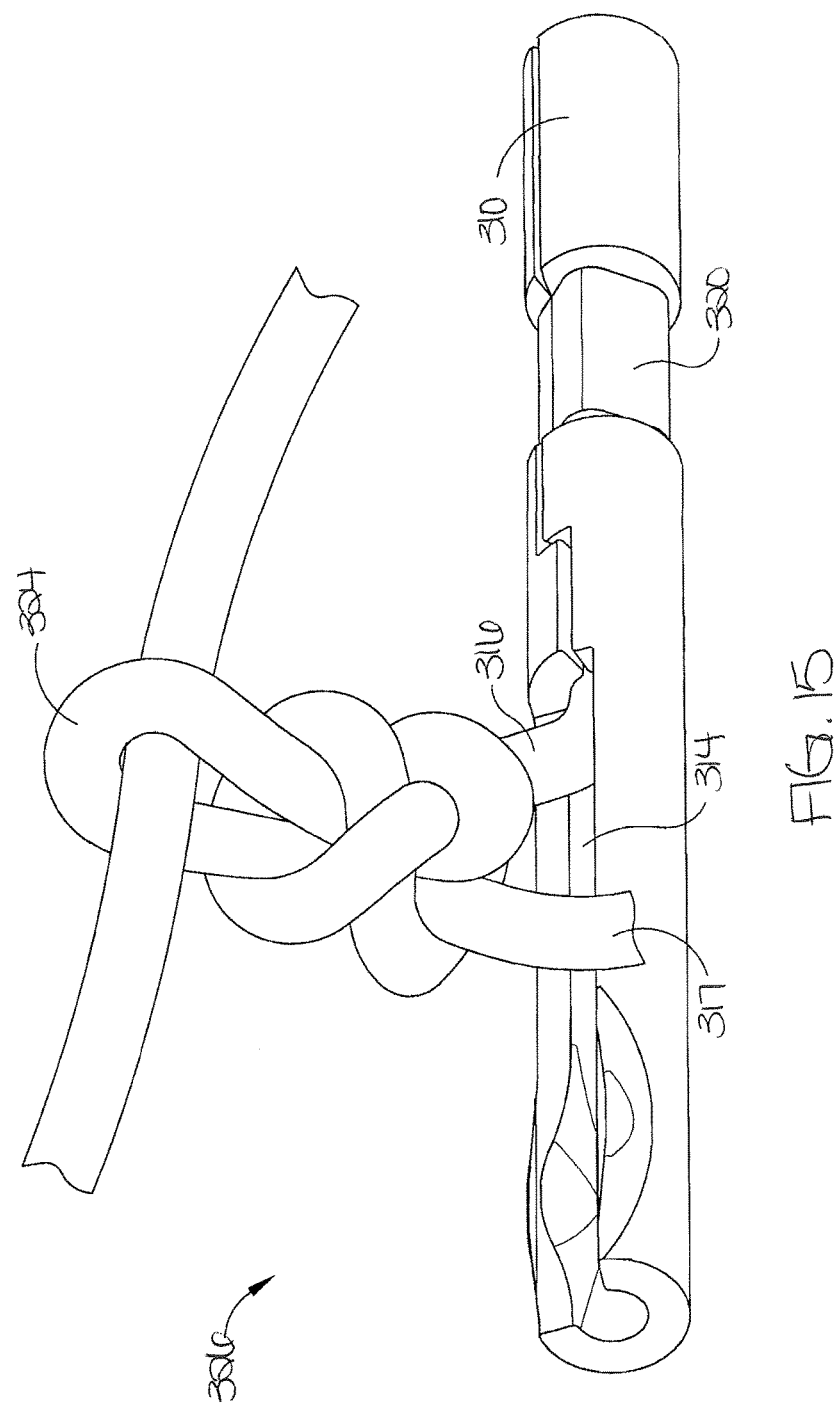

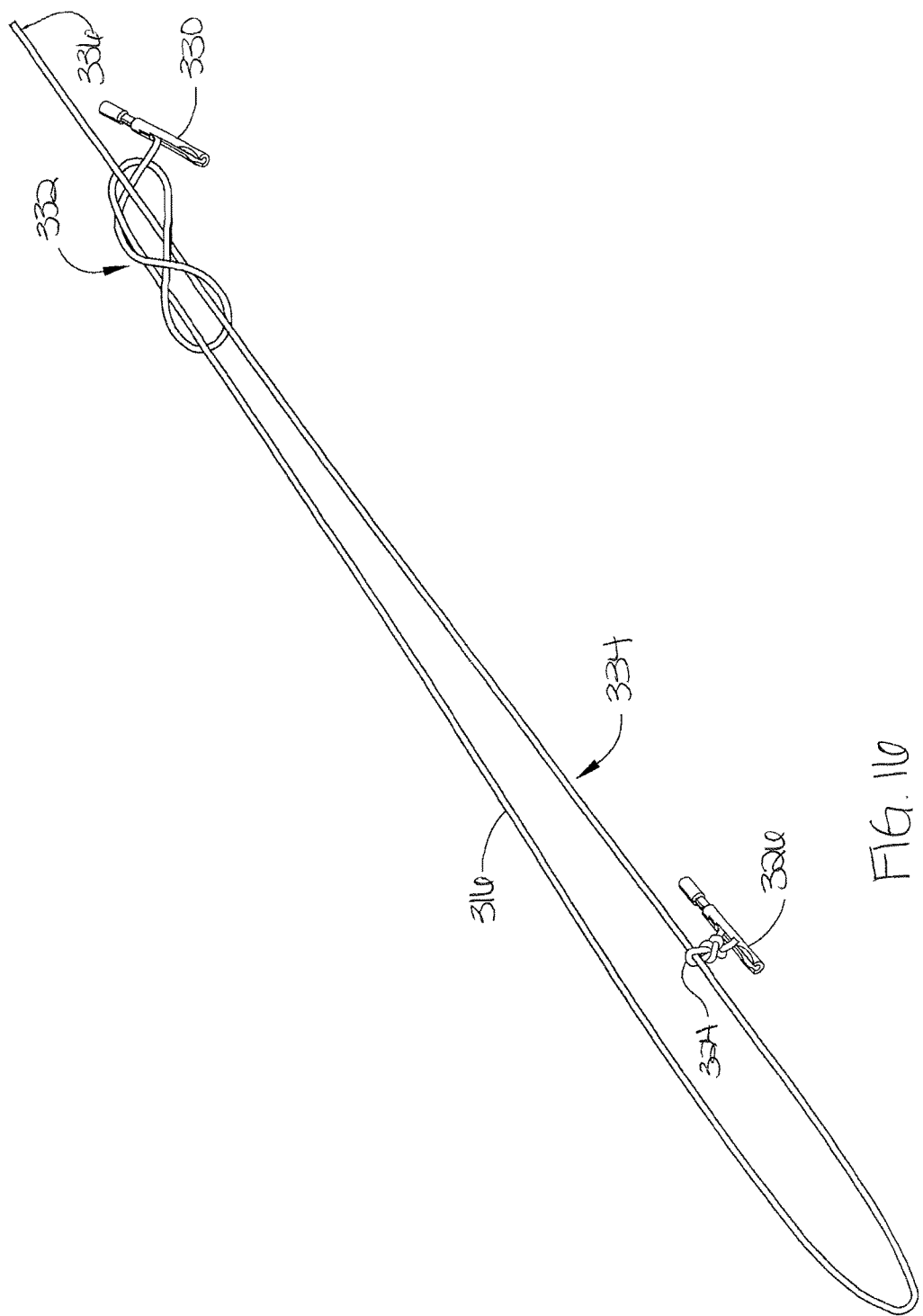

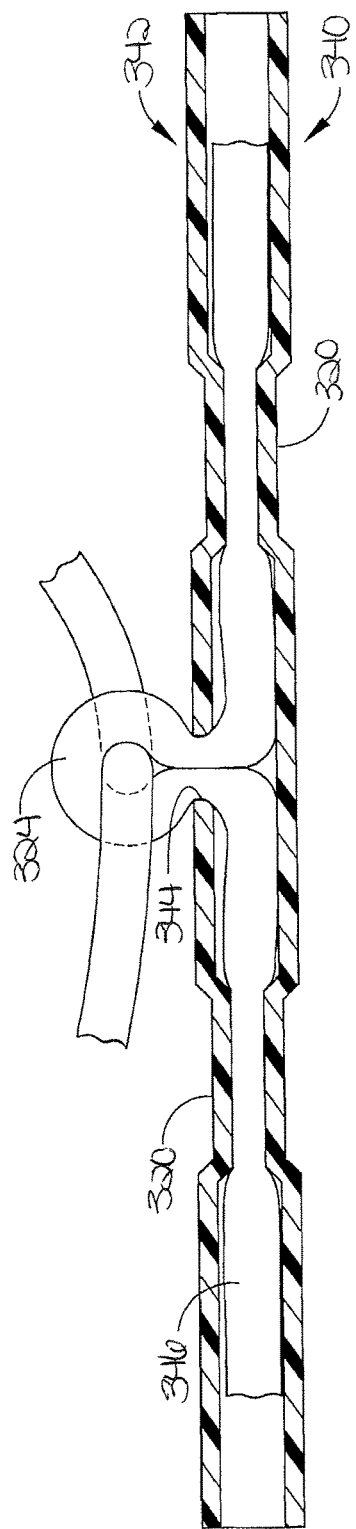

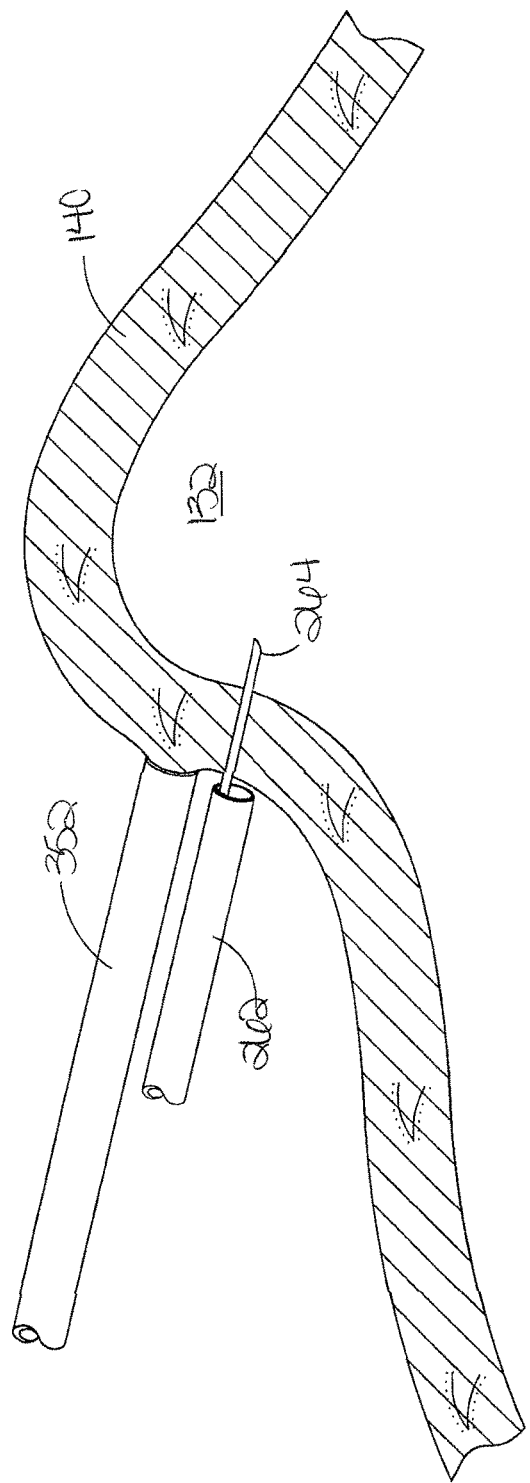

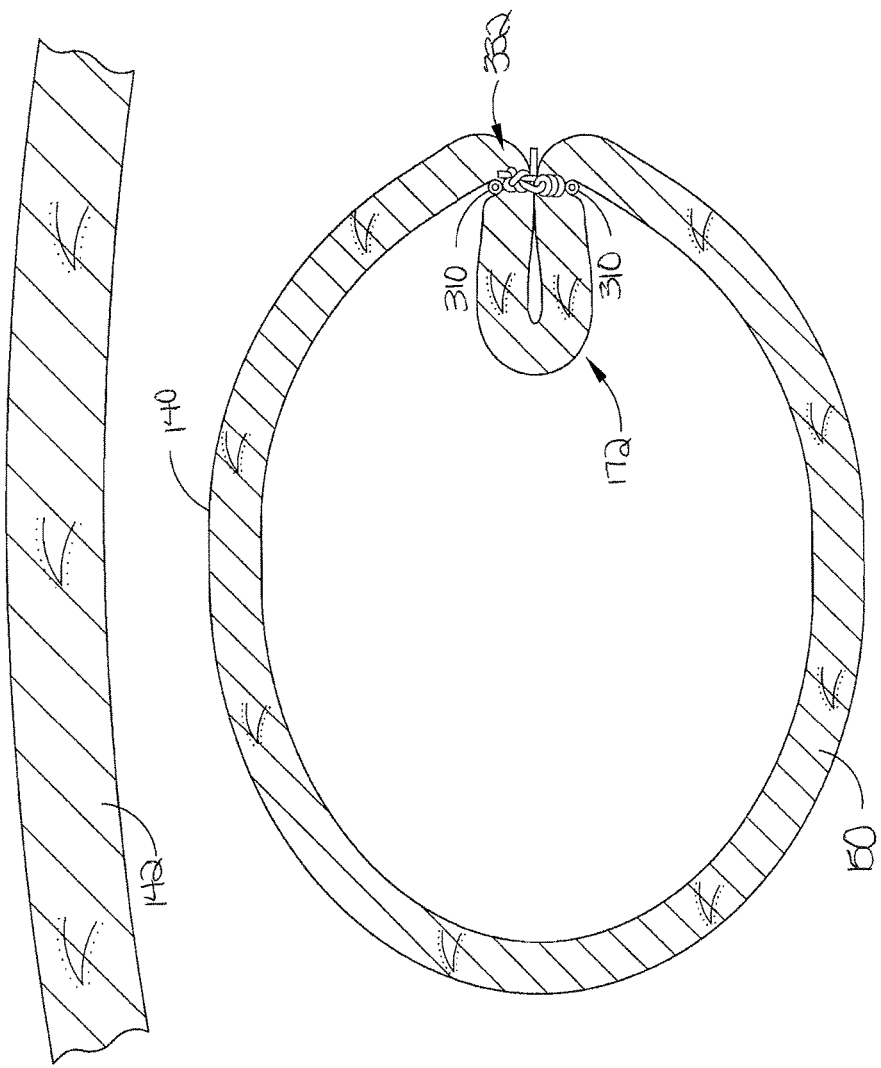

METHOD FOR GASTRIC VOLUME REDUCTION SURGERY

BACKGROUND OF THE INVENTION

1. Field of the Invention

The present invention relates generally to gastric reduction surgery and, more particularly, to a hybrid method for combining gastric volume reduction surgery with the application of a duodenal sleeve.

2. Description of the Related Art

Obesity is a medical condition affecting more than 30% of the population in the United States. Obesity affects an individual's personal quality of life and contributes significantly to morbidity and mortality. Obese patients, i.e. individuals having a body mass index ("BMI") greater than 30, often have a high risk of associated health problems (e.g., diabetes, hypertension, and respiratory insufficiency), including early death. With this in mind, and as those skilled in the art will certainly appreciate, the monetary and physical costs associated with obesity are substantial. In fact, it is estimated the costs relating to obesity are in excess of 100 billion dollars in the United States alone. Studies have shown that conservative treatment with diet and exercise alone may be ineffective for reducing excess body weight in many patients.

Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure a small stomach pouch is separated from the remainder of the gastric cavity and attached to a resectioned portion of the small intestine. This resectioned portion of the small intestine is connected between the "smaller" gastric cavity and a distal section of small intestine allowing the passage of food therebetween. The conventional RYGB procedure requires a great deal of operative time. Because of the degree of invasiveness, post-operative recovery can be quite lengthy and painful. Still more than 100,000 RYGB procedures are performed annually in the United States alone, costing significant health care dollars.

In view of the highly invasive nature of the RYOB procedure, other less invasive procedures have been developed. These procedures include gastric banding, which constricts the stomach to form an hourglass shape. This procedure restricts the amount of food that passes from one section of the stomach to the next, thereby inducing a feeling of satiety. A band is placed around the stomach near the junction of the stomach and esophagus. The small upper stomach pouch is filled quickly, and slowly empties through the narrow outlet to produce the feeling of satiety. Other forms of bariatric surgery that have been developed to treat obesity include Fobi pouch, bilio-pancreatic diversion and gastroplasty or "stomach stapling".

Morbid obesity is defined as being greater than 100 pounds over one's ideal body weight. For individuals in this category, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYOB or other complex procedures often outweigh the potential health benefits and costs. Accordingly, treatment options should involve a less invasive, lower cost solution for weight loss.

It is known to create cavity wall plications through endoscopic only procedures. However, operating solely within the interior of the gastric cavity limits the plication depth that can be achieved without cutting. Furthermore, access and visibility within the gastric and peritoneal cavities is limited in a purely endoscopic procedure as the extent of the reduction increases.

With the foregoing in mind, it is desirable to provide surgical weight loss procedures (and associated medical instruments) that are inexpensive, with few potential complications, and that provide patients with a weight loss benefit while buying time for the lifestyle changes necessary to maintain the weight loss. Further, it is desirable that the procedure be minimally invasive to the patient, allowing for a quick recovery and less scaring. The present invention provides such a procedure.

SUMMARY OF THE INVENTION

It is, therefore, an object of the present invention to provide a method for treating a patient including creating at least one incision to gain access to an peritoneal cavity, performing a gastric volume reduction procedure and introducing a device to prevent gastric contents from interacting with at least a portion of the duodenum.

It is also an object of the present invention to provide a method wherein the device is a duodenal sleeve.

It is another object of the present invention to provide a method wherein the duodenal sleeve includes a sleeve and a proximal end having a proximal opening with a self-expanding stent.

It is a further object of the present invention to provide a method wherein the sleeve is from about one foot to about five feet in length.

It is also an object of the present invention to provide a method wherein the step of introducing includes anchoring the proximal end to muscle in a pyloric portion of a stomach.

It is another object of the present invention to provide a method wherein the step of performing a gastric volume reduction procedure includes forming at least one fold of gastric tissue and securing the fold with a fastener.

It is a further object of the present invention to provide a method wherein the fold is on an exterior surface of the gastric cavity.

It is also an object of the present invention to provide a method the fold has serosa-to-serosa contact substantially along its entire length.

It is another object of the present invention to provide a method wherein the fold is formed in the anterior cavity wall.

It is a further object of the present invention to provide a method wherein the fastener is a tissue anchoring device.

It is also an object of the present invention to provide a method wherein the tissue anchoring device is a T-tag anchor.

It is another object of the present invention to provide a method wherein the step of folding includes physically abrading, or thermally or electrically damaging the gastric tissue.

It is another object of the present invention to provide a method wherein the fold is formed about the greater curvature of a stomach.

It is another object of the present invention to provide a method wherein the fastener is a staple.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a perspective view of a gastrointestinal implant device according to the principles of the present invention.

FIG. 2A is a sectional view of a body showing one embodiment of the gastrointestinal implant device implanted in the digestive system.

FIG. 3 is a perspective view of a catheter system for delivery of the gastrointestinal implant device.

FIG. 4 is a cross-sectional view of the inner shaft taken along line 4-4 of FIG. 3.

FIG. 5A is a plan view of the catheter system illustrating the collapsed stent stored inside the outer sheath of the gastrointestinal implant device.

FIG. 5B is a plan view of the catheter system illustrating the gastrointestinal implant device after release of the stent from the outer sheath.

FIG. 5C is a plan view of the catheter system illustrating the expanded gastrointestinal implant device after the sleeve retention wire has been released.

FIG. 14 is an isometric view of an exemplary T-Tag anchoring device FIG. 15 is a side view of the T-Tag anchoring device of FIG. 14, showing a first method for forming a suture loop.

FIG. 16 is an isometric view of a slip knot formed between a pair of T-Tag anchors, showing the knot in a loosened form.

FIG. 18 is a side view of a second exemplary T-Tag anchoring device, showing a second method for forming a suture loop.

FIG. 19 is a cross-sectional view of an isolated area of the gastric cavity wall during a needle insertion.

FIG. 29 is a cross-sectional view of a gastric cavity showing T-Tag anchors deployed into the anterior and posterior cavity walls.

FIG. 30 is a cross-sectional view of a gastric cavity similar to FIG. 29, showing the anterior and posterior walls cinched together into a fold.

DESCRIPTION OF THE PREFERRED EMBODIMENTS

Figure 2B:
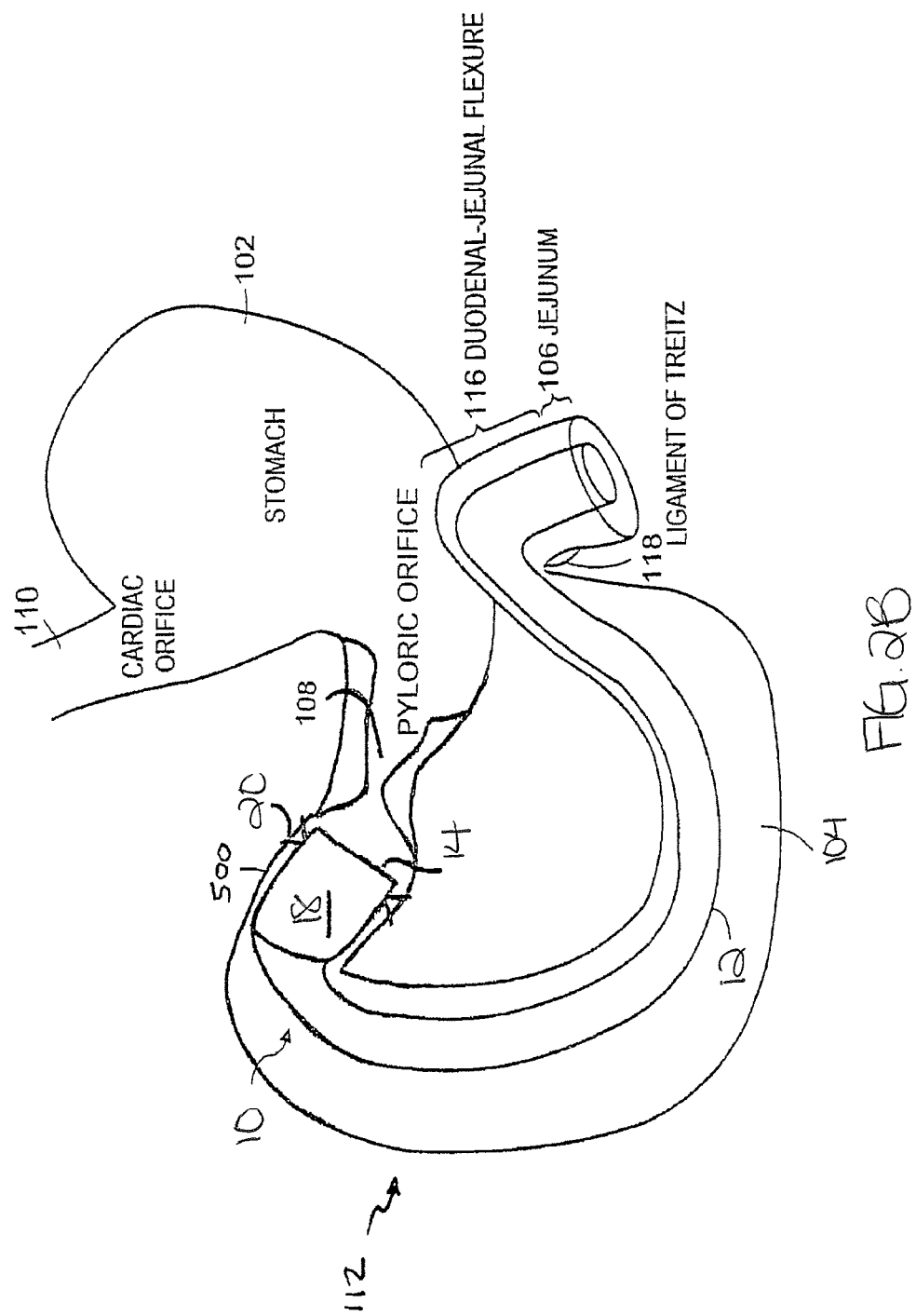
FIG. 2B is a sectional view of a body showing an alternative embodiment of the gastrointestinal implant device implanted in the digestive system.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Gastric volume reduction, otherwise referred to as "Reduction Gastroplasty", is a procedure that reduces stomach capacity which in turn may reduce the amount of food a patient may eat. While many believe the mechanism of action is purely restrictive, the present invention employs multiple mechanisms working together to cause changes in the metabolic balance leading to weight loss. By combining multiple treatment mechanisms the following changes in physiology are noted: gastrointestinal motility, gastric emptying, rapid onset/decline of gastrointestinal hormone levels, excluding regions of the stomach from mechanical stretch, etc.

By combining gastric volume reduction procedures with a duodenal sleeve, such as, that marketed by GI Dynamics under the tradename EndoBarrier, improved bariatric treatment is achieved. As will be discussed below in greater detail, a duodenal sleeve is a device that is delivered transorally and is preferably anchored in the vicinity of the pylorus of the stomach. Attached distal to the anchor is a long flexible sleeve (~2 feet in length). When in place food goes directly from the stomach into the sleeve without coming into contact with the duodenum. Bile from the common bile duct is permitted to enter the duodenum freely, but does not come in contact with food until it reaches the end of the sleeve. This exclusion of gastric contents is theorized to reduce absorption and has been shown clinically to cause weight loss as well as rapid (<1 week) remission of type 2 diabetes. The combination of gastric volume reduction and a duodenal sleeve seeks to mimic a RYGB in that there is a significant reduction in gastric capacity coupled with a malabsorptive component.

The present procedure is achieved by deploying a duodenal sleeve as described below. Thereafter a gastric volume reduction procedure (as described below for either anterior surface plication or greater curvature invagination) is performed. The method for treating a patient in accordance with the present invention generally includes creating at least one incision to gain access to the peritoneal cavity, forming at least one fold on the exterior of the gastric tissue through the incision, the fold having serosa-to-serosa contact substantially along its entire length, securing the fold with a fastener, and introducing a device to prevent gastric contents from interacting with at least a portion of the duodenum.

With regard to the initial deployment of a duodenal sleeve (or gastrointestinal implant device 10), and with reference to FIG. 1, a gastrointestinal implant device 10 for use in accordance with the present invention is shown. The gastrointestinal implant device 10 includes an elongated open-ended flexible sleeve or tube 12 having a first proximal opening 14 and a second distal opening 16. Within the sleeve 12 is a passageway that extends from the first proximal opening 14 to the second distal opening 16 for transporting the chyme exiting the stomach. The surface of the passageway (the interior surface of the gastrointestinal implant device 10) is smooth to enable the chyme to easily pass through. The exterior surface of the gastrointestinal implant device 10 is smooth to prevent tissue in-growth and to be non-irritating to the bowel.

Within the gastrointestinal implant device 10 at the proximal end including the first proximal opening 14 is a collapsible self-expanding stent 18. The stent 18 includes a plurality of opposed barbs 20 for anchoring the gastrointestinal implant device 10 to the muscular pylorus in the stomach 102.

The sleeve material is thin and conformable so that it collapses in the intestine to a small volume to minimize bowel irritability. It has a low coefficient of friction (<0.20) so that chyme slides easily through it and the bowel slides easily around it. It is of low permeability to fluids so that the chyme does not touch the bowel wall and the digestive enzymes do not significantly breakdown the chyme. It is biologically inert and non-irritating to the tissues. One such material is expanded polytetrafluoroethylene (ePTFE), a fluoropolymer, with a wall thickness of about 0.006" and an internodal distance of 20 microns. This material is hydrophobic but is slightly porous. However, these very small pores may plug over time. The porosity may be reduced by coating the material on the inside, outside or in the pores with dilute solutions of silicone or polyurethane. Another material is polyethylene with a wall thickness of less than 0.001". Rubber-like materials typically have friction coefficients of 1-4, significantly stickier than these materials. However, in alternate embodiments other materials having similar characteristics can be used.

The sleeve 12 includes two layers of material at least at the proximal end. A first outer layer covers the exterior of the stent. The second inner layer covers the interior surface of the stent 18. The barbs 20 protrude from the exterior surface of the stent 18 through the first outer layer of the sleeve 12. The holes in the first outer layer through which the barbs 20 protrude are filled with an impervious material such as silicone or urethane to limit mixing of digestive juices with the chyme flowing through the passageway. The diameter of the sleeve 12 is selected such that the first outer layer of the sleeve 12 fits over the stent 18.

The sleeve length 22 ranges from about one foot to about five feet. The typical length of the sleeve 12 is about 1.5 feet from the anchor (barbs 20) in the pyloric region of the stomach to below the ligament of Treitz. The length 22 of the sleeve 12 is selected to bypass the duodenum and a portion of the jejunum. The length is increased to further decrease absorption by bypassing a longer section of the jejunum. The length 22 of the sleeve 12 is variable and dependent on the patient's Body Mass Index (BMI).

The covered stent 18 can be collapsed into a sheath having a diameter less than ¼ inch to enable endoscopic delivery. Covering the exterior surface of the stent 18 with the first outer layer of the sleeve 12 permits endoscopic removal of the gastrointestinal implant device 10 by preventing tissue in-growth on the exterior surface of the stent 18.

Referring to FIG. 2A, the gastrointestinal implant device 10 is shown implanted in the digestive system. The first proximal opening 14 of the gastrointestinal implant device 10 is anchored to muscle in the pyloric portion of the stomach 102. The barbs 20 grip onto the muscle to anchor the gastrointestinal implant device 10 in place so that the gastrointestinal implant device 10 can not be dragged into the stomach or down into the intestines with movement of the stomach and the intestines. FIG. 2B is a sectional view of a body showing an alternative embodiment of the gastrointestinal implant device 200 implanted distal to the pylorus 108.

The sleeve 12 extends over the ligament of Treitz 118 beyond the proximal jejunum. Extending the sleeve below the ligament of Treitz reduces the likelihood that the sleeve will move back through the duodenum 104 toward the stomach 102.

After the gastrointestinal implant device 10 has been placed in the body and anchored in either the pyloric portion of the stomach or distal to the pylorus 108, chyme leaving the stomach passes through passageway inside the sleeve 12 and bypasses the duodenum 104 and proximal jejunum 106. By directing the chyme through the sleeve 12 the digestion and the absorption process in the duodenum 104 is interrupted. By interrupting mixing of the chyme with juices in the duodenum 104, partially digested food material is not broken down into particles small enough to be absorbed by the body. Further, there is no mixing of bile with the chyme until the chyme reaches the jejunum 106. The absorption of fats and carbohydrates is reduced by delaying the mixing of bile with the chyme.

The pyloric valve opens periodically to allow chyme to exit the stomach 102 to the duodenum 104. In one embodiment of the invention the length of the stent 18 is selected to keep the pyloric valve permanently open to induce "dumping syndrome". By keeping the pylorus 108 open, the chyme empties rapidly into the sleeve 12 and passes down through the sleeve 12 and into the jejunum 106 with minimal digestion. This results in a "dumping syndrome" which is a reaction to excessive rapid dumping of chyme into the jejunum 106 causing the patient to feel ill, dizzy and nauseated. This syndrome is particularly enhanced when sugars and carbohydrates are eaten and passed directly into the jejunum 106.

To hold the pyloric valve open, the length of the stent 18 should be at least 1.5 inches so that the stent 18 extends from the anchoring position in the pyloric portion of the stomach through the pyloric orifice 108 (the opening from the stomach while the pyloric valve is open). The length of the stent is selected so that the distal end of the stent is above the papilla of Vater. As shown, the stent 18 extends through the pyloric orifice 108 to hold the pyloric valve permanently open. In an alternative embodiment, the length of the stent 18 is selected such that the stent 18 ends at the stomach side of the pyloric orifice 108 allowing the pyloric valve to operate normally.

The sleeve 12 provides weight loss mechanisms by providing negative feedback, reduced fat digestion and reduced desire for food. The reduced fat digestion occurs because the sleeve 12 delays the mixing of bile and pancreatic juices with chyme from the stomach until after the chyme leaves the sleeve. The reduced desire for food may occur because the sleeve 12 blocks hormonal release from the duodenum.

After the chyme from the stomach has passed through the sleeve, the sleeve becomes extremely thin and floppy, permitting the sleeve to contour to the inner walls of the intestine. The sleeve is non-compliant and drapes away from the intestinal walls thereby permitting the pancreatic juice to flow unimpeded into the duodenum through the papilla of Vater. The normal peristalsis of the bowel is used to propel the chyme through the intestines.

The gastrointestinal implant device 10 is designed for endoscopic placement. FIG. 3 is a perspective view of a portion of a catheter system 24 for delivery of the gastrointestinal implant device. The catheter system follows a guide wire 34 through the esophagus and the stomach to the pylorus portion of the stomach. The guide wire 34 enters a first inner lumen at the proximal end 30 of the catheter system 24 and exits the first inner lumen at the distal end 40 of the catheter system 24.

The catheter system 24 includes an outer sheath 26 for storing the stent 18 in collapsed form, a flange 38 to pull back the outer sheath 26 and a sleeve retention wire release mechanism 36 for releasing a sleeve retention wire 32 from the proximal end of the flexible sleeve 12 after the stent has been released from the outer sheath 26.

As described in conjunction with FIG. 1, the distal portion of the gastrointestinal implant device includes a flexible sleeve 12 which can negotiate the duodenum and the jejunum. A sleeve retention wire 32 travels through a second inner lumen and exits the second inner lumen to secure the distal end of the sleeve 12 to an inner sheath 44. The sleeve retention wire 32 is coupled to the sleeve retention wire release mechanism 36 for releasing the sleeve retention wire 32 after the gastrointestinal implant device has been positioned in the pyloric section of the stomach. The release mechanism 36 will be described later in conjunction with FIG. 5A.

The sleeve 12 is secured temporarily outside the inner sheath 44 allowing for proper positioning of the gastrointestinal implant device and then for release. As shown, the sleeve 12 is secured by the sleeve retention wire 32 using a dead-bolt mechanism 28. Non-stick coatings such as Teflon on the sleeve retention wire 32 are preferred to make release easier to accommodate tortuous anatomical pathways. The sleeve retention wire 32 extends through the second inner lumen from the release mechanism 36 of the catheter system 24 to the dead-bolt mechanism 28. The dead-bolt mechanism 28 is described later in conjunction with FIG. 4. The sleeve retention wire 32 holds the sleeve in position. The distal end of the folded sleeve is released by the release mechanism 36 by pulling the sleeve retention wire 32 backward from the proximal end 30 of the catheter.

The proximal portion of the gastrointestinal device includes a covered stent. The covered stent does not enter the duodenum and thus is stiffer than the sleeve because it remains in the pylorus of the stomach. The stent in the gastrointestinal implant device is collapsed and stored in the outer lumen within the outer sheath 26 between the flange 38 and the distal end of the outer sheath 26. The stent is supported in a collapsed form by the outer sheath 26. The catheter system 24 is inserted into the digestive system through the esophagus to the pyloric section of the stomach. The proximal end of the outer sheath 26 is positioned in the stomach, in the pylorus through the use of positioning ring 42. After the outer sheath 26 has been positioned, the stent is retracted from the outer lumen of the catheter by pulling flange 38 toward the proximal end of the catheter system 24. Upon release, the stent self-expands by its own elastic restoring force to engage the anchor portion with the stomach muscle at the pyloric section of the stomach.

FIGS. 5A-5C illustrate a method for delivery of the gastrointestinal implant device. FIG. 5A is a plan view of the catheter system illustrating the collapsed stent stored inside the outer sheath 26 of the gastrointestinal implant device. As described in conjunction with FIG. 3, the stent 18 is stored inside the outer sheath and the distal end of the sleeve 12 is secured outside the inner sheath 44 by a sleeve retention wire 32.

FIG. 5B is a plan view of the catheter system 24 illustrating the gastrointestinal implant device after release of the stent 18 from the outer sheath 26. The flange 38 has been pulled back toward the proximal end of the catheter system 24 to pull back the outer sheath 26 from the stent and the stent 18 has self-expanded. The sleeve retention wire 32 holds the distal end of the sleeve 12.

Once in place, the sleeve retention wire 32 can be removed. As described previously in conjunction with FIG. 3, the sleeve retention wire 32 is coupled to release mechanism 36. Handle 48 in the release mechanism 36 acts as a pivot device to pull the sleeve retention wire 32 from the dead-bolt mechanism 28. The distal end of the gastrointestinal implant device is released by moving handle 48 in a clockwise direction 50. As the handle 48 is moved in direction 50, the sleeve retention wire 32 threaded through the folds of the sleeve is pulled back through the second inner lumen 46 and disengages from the sleeve at the distal end of the gastrointestinal implant device. The sleeve retention wire 32 extends from the distal end of the gastrointestinal implant device through the second inner lumen 46. The wire is connected to the handle 48 at the proximal end of the catheter.

FIG. 5C is a plan view of the catheter system illustrating the expanded gastrointestinal implant device after the sleeve retention wire has been released. The handle 48 has been moved in a clockwise direction and the sleeve retention wire 32 has been pulled back through the second inner lumen 46 to release the distal end of the sleeve 12.

The gastrointestinal implant device offers a new alternative where other means of weight loss and efforts at behavior modification have failed. Because the gastrointestinal implant device is endoscopically introduced, there is a reduced risk at insertion compared to surgery. The procedure is also completely reversible, making this approach an ideal solution for patients who are desperate to reverse behavioral patterns that have lead to weight gain.

When inserted in the body, the gastrointestinal implant device mimics the duodenal bypass of the Roux-en-Y procedure. The implanted device reduces caloric absorption by delaying enzyme mixing with food and provides the feedback produced by the Roux-en-Y procedure by producing dumping syndrome when high sugar meals are ingested. Rapid stomach emptying is encouraged by inserting a stent in the pylorus to hold the pylorus open and all food bypasses the duodenum and passes rapidly into the jejunum. The implant device is an improvement on the Roux-en-Y procedure because it is minimally invasive and reversible. In the treatment of the super-obese where aggressive weight loss is not achieved, the length of the implant device below the stent can be further increased to drive the patient close to the point of malabsorption.

Figure 6:
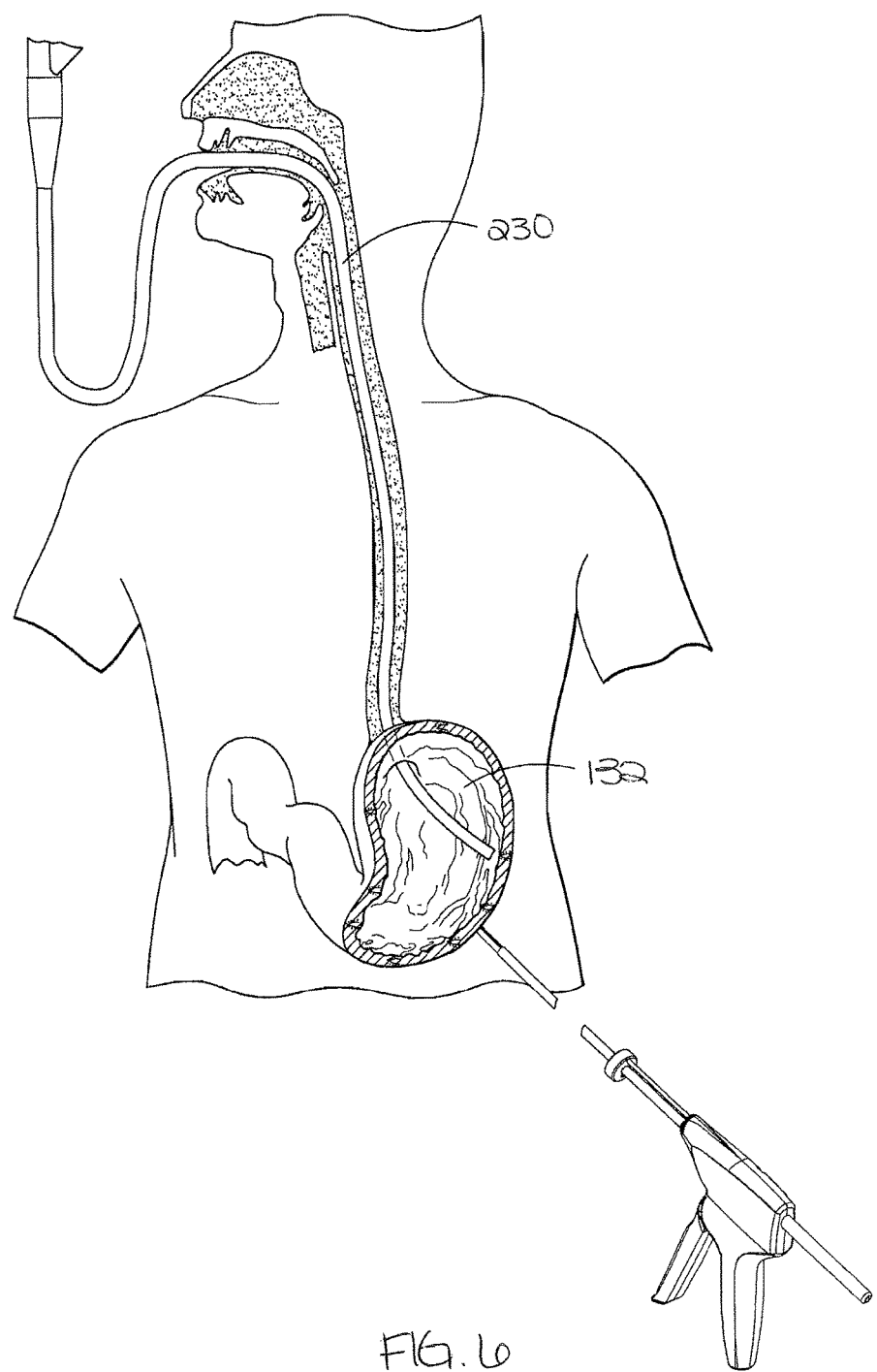
FIG. 6 is a schematic view of a patient during a hybrid endoscopic-laparoscopic procedure.

As discussed above, once the gastrointestinal implant device is properly positioned (or before the gastrointestinal implant device is deployed), gastric volume reduction is implemented. In accordance with a preferred embodiment of the present invention, gastric volume reduction is achieved in accordance with the procedures and medical instruments disclosed in commonly owned U.S. patent application Ser. No. 11/779,314, entitled "HYBRID ENDOSCOPIC/LAPAROSCOPIC DEVICE FOR FORMING SEROSA TO SEROSA PLICATIONS IN A GASTRIC CAVITY", filed Jul. 18, 2007, which is incorporated herein by reference. Referring to FIG. 6 is a diagrammatic view of a patient during a hybrid endoscopic-laparoscopic procedure. In the method of the present invention, folds are formed in the gastric cavity wall through a hybrid laparoscopic-endoscopic approach. In the hybrid approach, visualization of the one or more fold locations can be achieved by passing an endoscope into the interior of the gastric cavity. As shown in FIG. 6, a flexible endoscope 230 can be passed transesophagealy into the gastric cavity 132. Endoscope 230 provides insufflation, illumination, and visualization of gastric cavity 132, as well as a passageway into the gastric cavity. Gastric cavity 132 is insufflated through endoscope 230 to create a sufficiently rigid working surface that may be pierced without damaging the opposing wall of the cavity. Insufflation of the gastric cavity also allows the boundaries of the cavity and the desired location for a fold to be mapped out by external palpation of the abdomen. The pressure on the abdominal wall is observed within gastric cavity 132 through endoscope 230 and may aid in determining the appropriate placement of one or more trocars, or other type of port allowing abdominal, laparoscopic access. Using endoscope 230 to visualize the plication locations may reduce or eliminate the need for visualization on the outside of the cavity.

Figure 7:
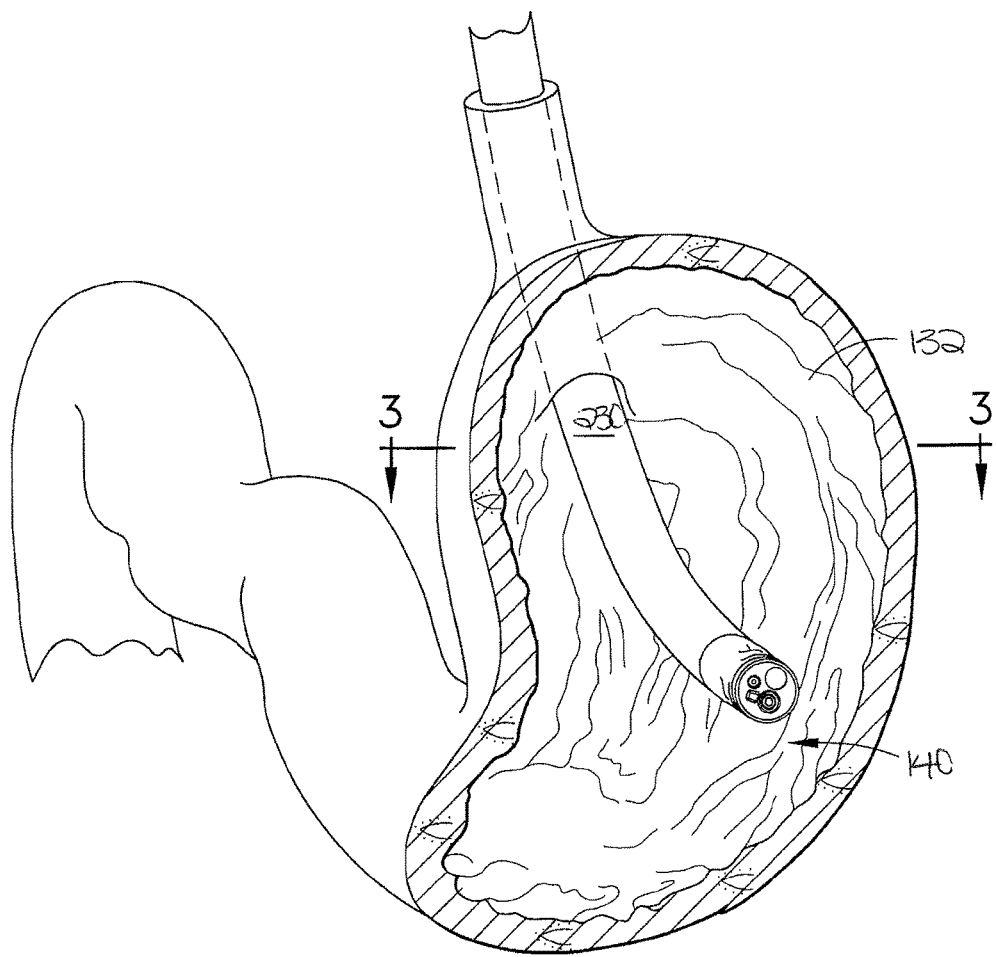
FIG. 7 is a diagrammatic, exterior view of a gastric cavity, partially broken way to show an endoscope positioned against the interior surface of the anterior cavity wall.
Figure 8:
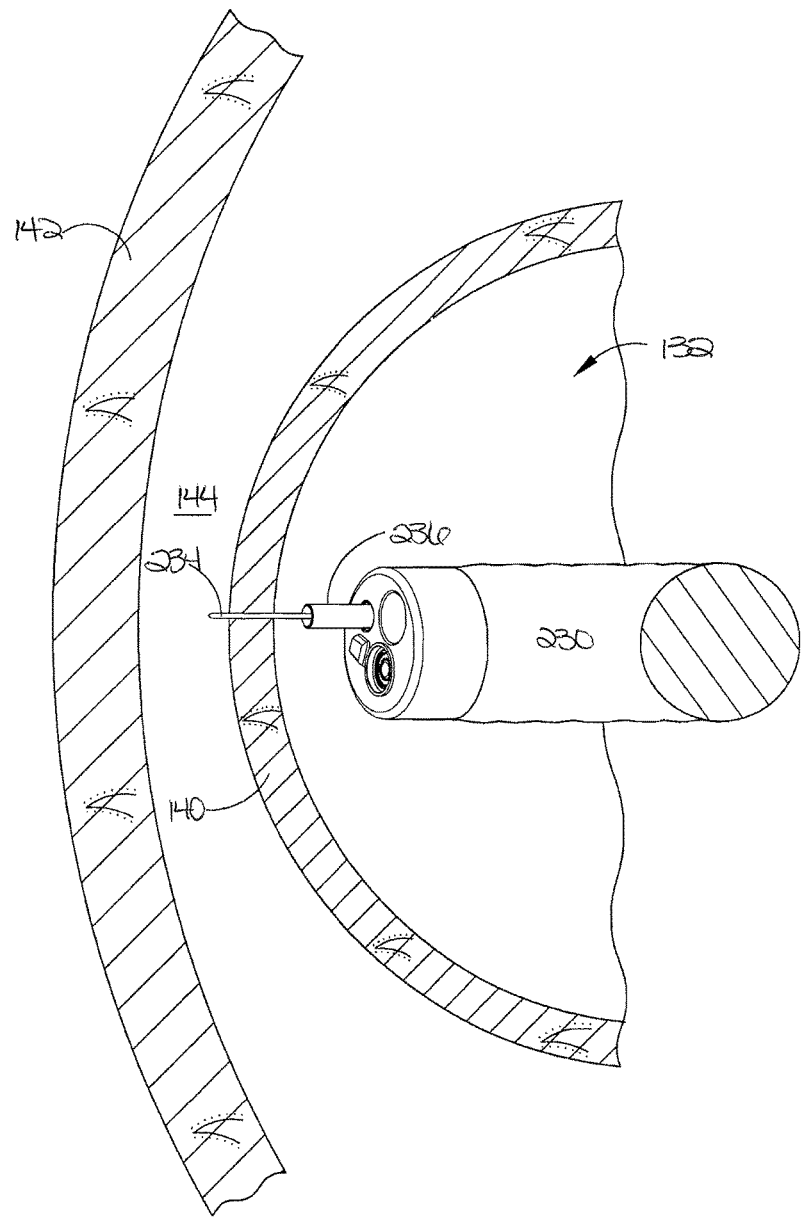
FIG. 8 is a cross-sectional view of an abdominal wall and gastric cavity showing a needle inserted through the gastric cavity wall into the peritoneal cavity.

Eliminating the need to visualize the outside of the gastric cavity also reduces or eliminates the need to insufflate the abdominal cavity. However, where deemed necessary, the abdominal cavity may be insufflated prior to placement of a trocar to expand the working area inside the cavity. Typically, the abdominal cavity is insufflated using a Veress needle that is inserted at the umbilicus or left upper quadrant of the cavity in order to introduce carbon dioxide ($CO_2$) into the cavity. Although common practices involve using a Veress needle to create additional working space in the abdominal cavity for safer trocar insertion, it introduces a small risk of organ perforation or infection due to the lack of guidance in inserting the needle. An alternative method to potentially reduce this risk involves transorally insufflating the abdomen by inserting a shielded needle into the working channel of endoscope 230 prior to passage of the scope into the gastric cavity. Inside gastric cavity 132, the endoscope 230 is pointed towards the distal anterior surface of the cavity, as shown in FIG. 7. The needle 234 is extended out the distal end of endoscope 230, and a protective shield 236 withdrawn from the needle tip, so that the needle can be inserted through the anterior cavity wall 140, as shown in FIG. 8. Needle 234 is inserted to a position between anterior cavity wall 140 and the abdominal wall 142. The distal anterior surface of the gastric cavity is a desirable area to puncture with the needle due to the absence of critical organs in this area. With needle 234 outside of the cavity wall, a suitable abdominal insufflation gas such as $CO_2$ is pumped through the needle and into the peritoneal cavity 144 to provide an area within the cavity to insert the trocar.

Figure 9:
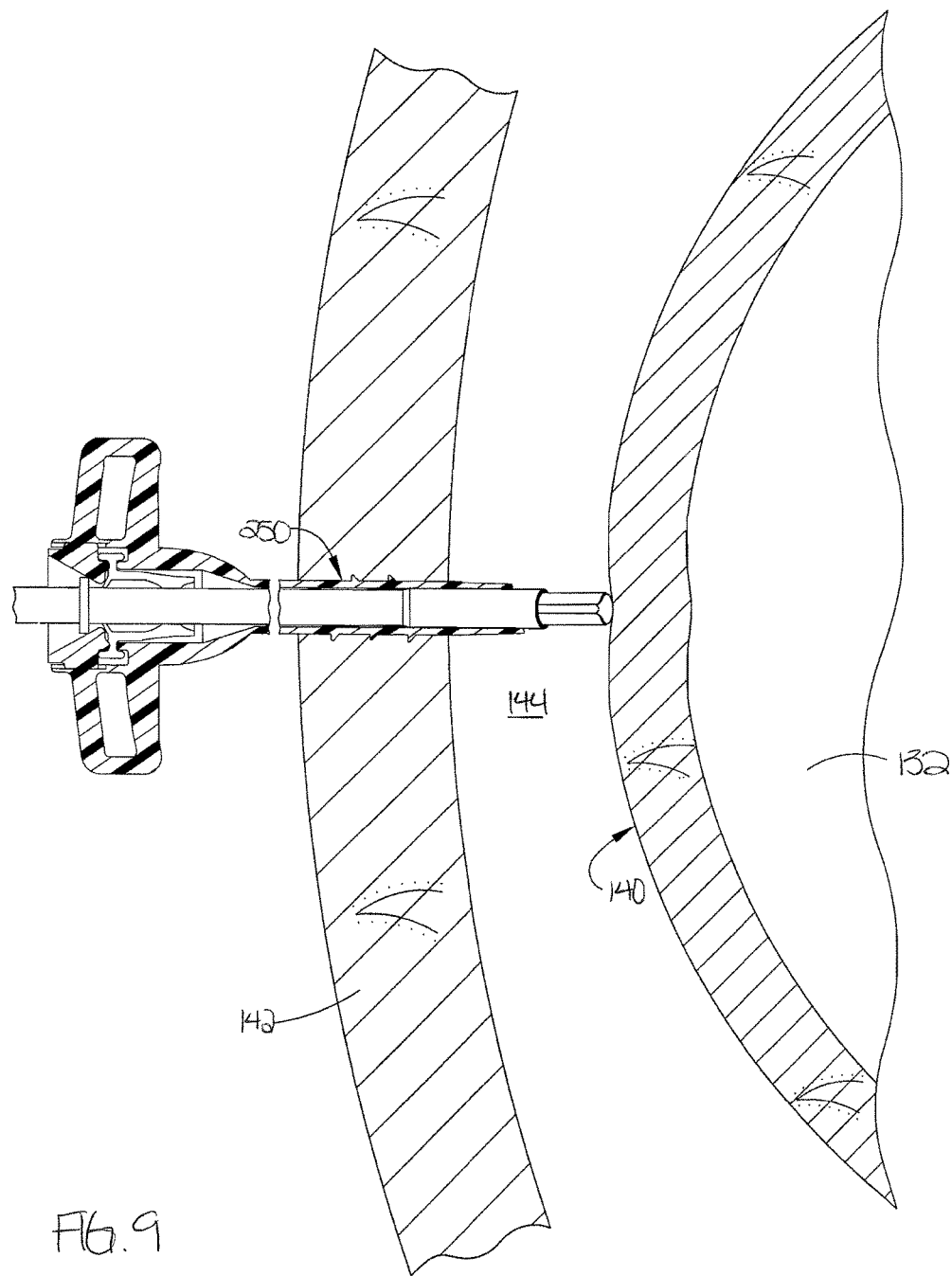
FIG. 9 is a cross-sectional view of an abdominal wall and gastric cavity showing a laparoscopic device probing tissue within the peritoneal cavity.

After the gastric cavity has been mapped through the endoscope, and the abdominal cavity insufflated if necessary, a trocar is inserted into the abdominal wall to provide access to the peritoneal cavity. FIG. 9 shows a trocar 250 inserted through an incision in abdominal wall 142. Trocar 250 is inserted directly above gastric cavity 132. The placement of trocar 250 will depend upon the intended location of the fold. Trocar 250 preferably has a small diameter to allow an adequate passageway for instruments while minimizing the size of the incision. Trocars with diameters in the range of 3-5 mm provide suitable access to the cavity. Percutaneous approaches with device diameters less than 3-5 mm remain a possibility however, with the size of the hole defined by the diameter of the anchor (if penetrating anchors are used) or the diameter of the piercing needle. With trocar 250 inserted into abdominal wall 142, a suture anchor deployment device is passed through the trocar and into the peritoneal cavity 144 to facilitate and secure a fold.

Figure 10:
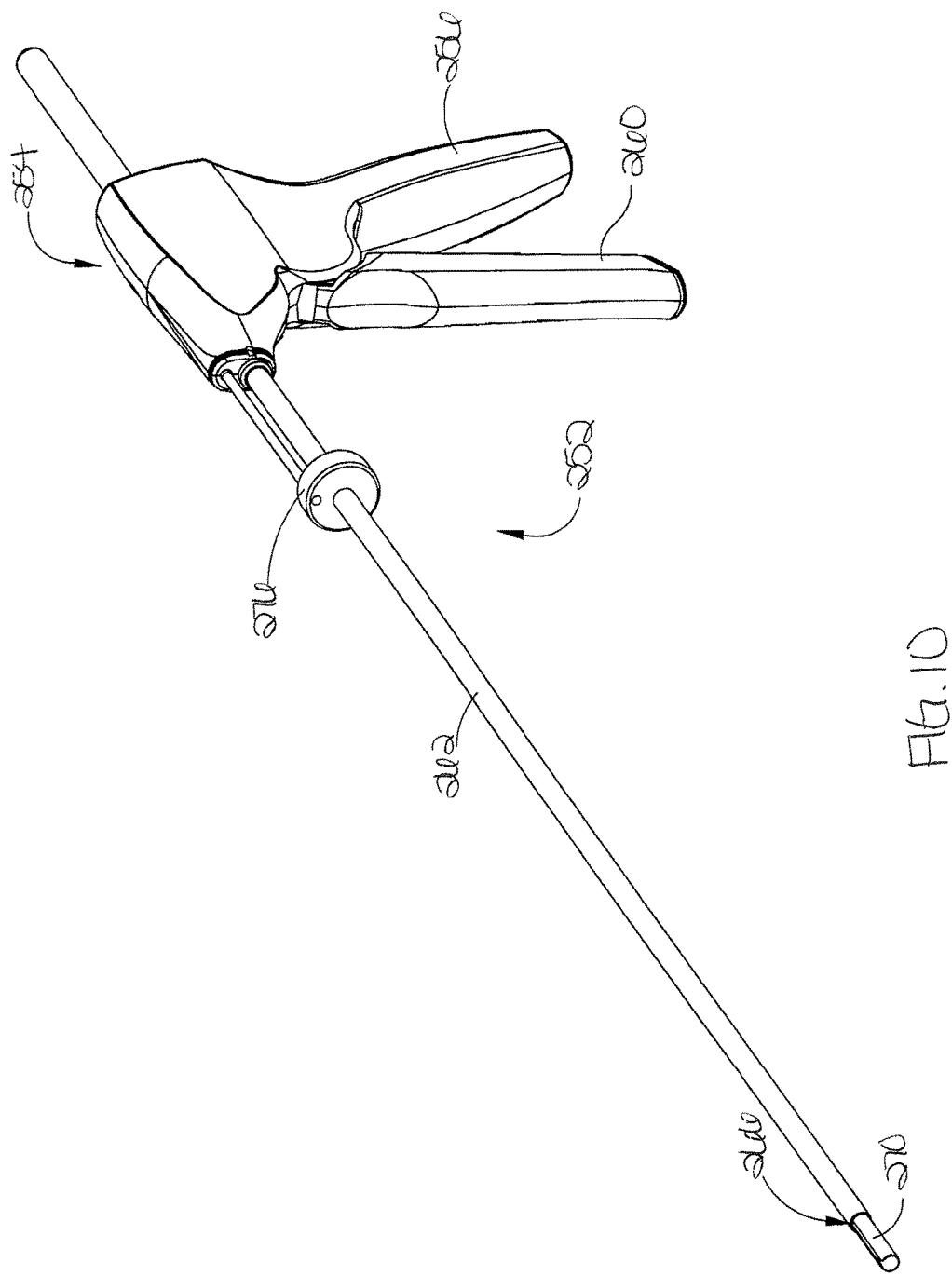
FIG. 10 is an isometric view of an exemplary suture anchor deployment device.

FIG. 10 illustrates an exemplary suture anchor deployment device 252 for use during a cavity wall folding procedure. The exemplary device shown and described below deploys multiple T-Tag type suture anchors for facilitating a tissue fold. However, T-Tag type suture anchors are only one of numerous types of tissue fasteners that can be utilized for forming a cavity wall fold. Various other tissue fasteners which are suitable for apposing and securing tissue such as, for example, simple suture knots and laparoscopically deployable suture anchors, may also be utilized without departing from the scope of the invention. As one skilled in the art will recognize, examples of fasteners suitable for this task include but are not limited to the T-type anchors (mentioned above and described in more detail below), reconfigurable "basket"-type anchors (which generally comprise a number of configurable struts or legs extending between two collars or support members), and linear anchors (elongate anchors which are configured to fold or become compressed into a bowed or expanded configuration). In general, anchor characteristics are such that prior to deployment they can easily be placed into or through tissue(s), but after deployment, have an altered configuration providing at least one dimension sufficiently large to maintain the anchor in place. As shown in FIG. 10, the exemplary deployment device includes a handle 254 having a pistol grip 256 and a movable trigger 260. An elongated, tubular deployment device housing 262 extends distally from handle 254. Deployment device housing 262 has sufficient length (on the order of 18") to enable use within an obese patient at numerous trocar access sites. Likewise, deployment device housing 262 is sized to allow for passage through a small (3-5 mm) diameter trocar.

It is also envisioned that the fastener does not completely penetrate the gastric wall. Partial thickness fasteners such as staples (e.g., 'box style' staples, 'B' form stables, 'ring form' staples, etc.), barbed anchors, hooks, some T-Tag variants, etc. may also be used to secure tissue apposition optionally allowing for serosa-to-serosa healing to occur.

Figure 11A:
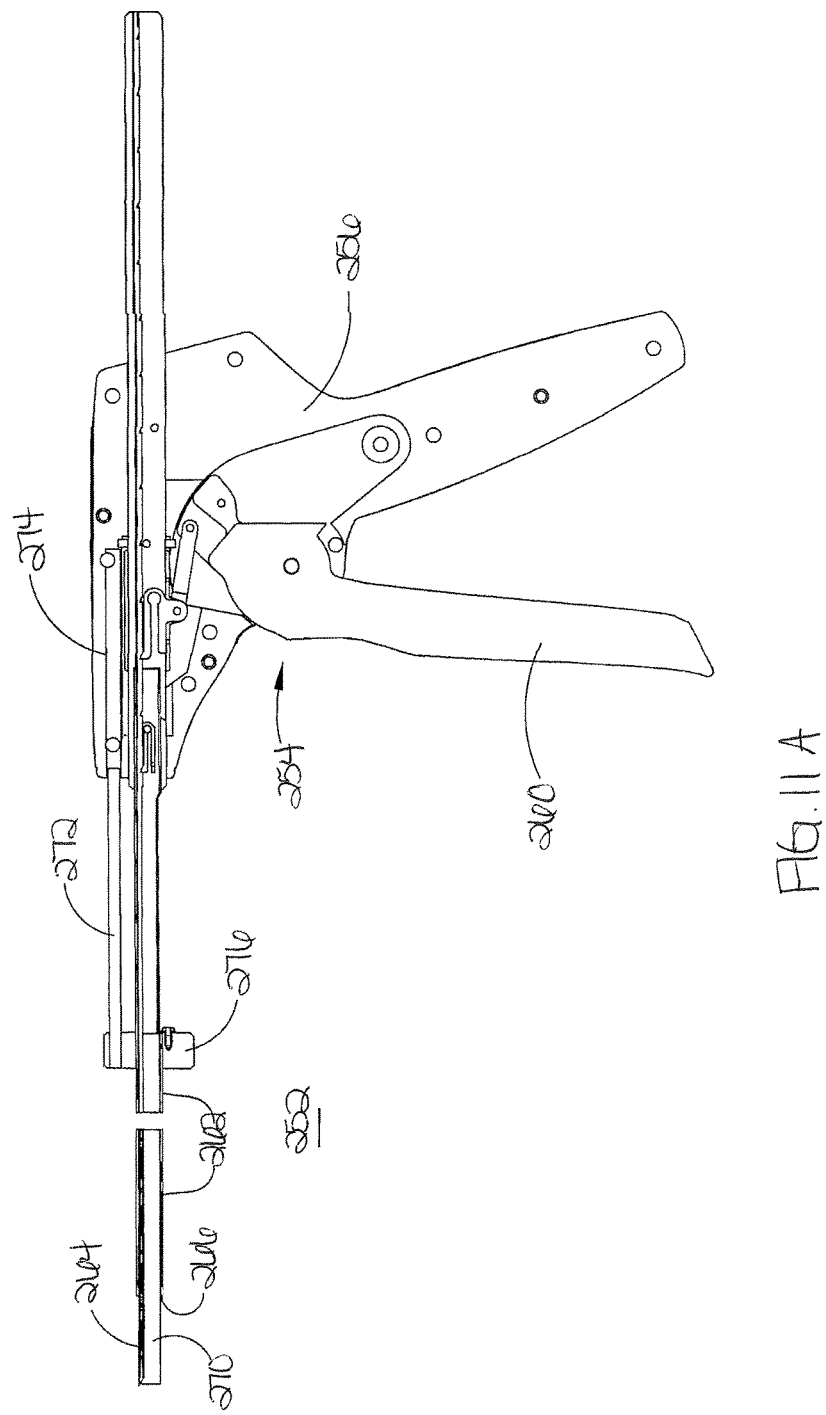
FIGS. 11A and 11B are side cross-sectional views of the suture anchor deployment device shown in FIG. 10.
Figure 11B:
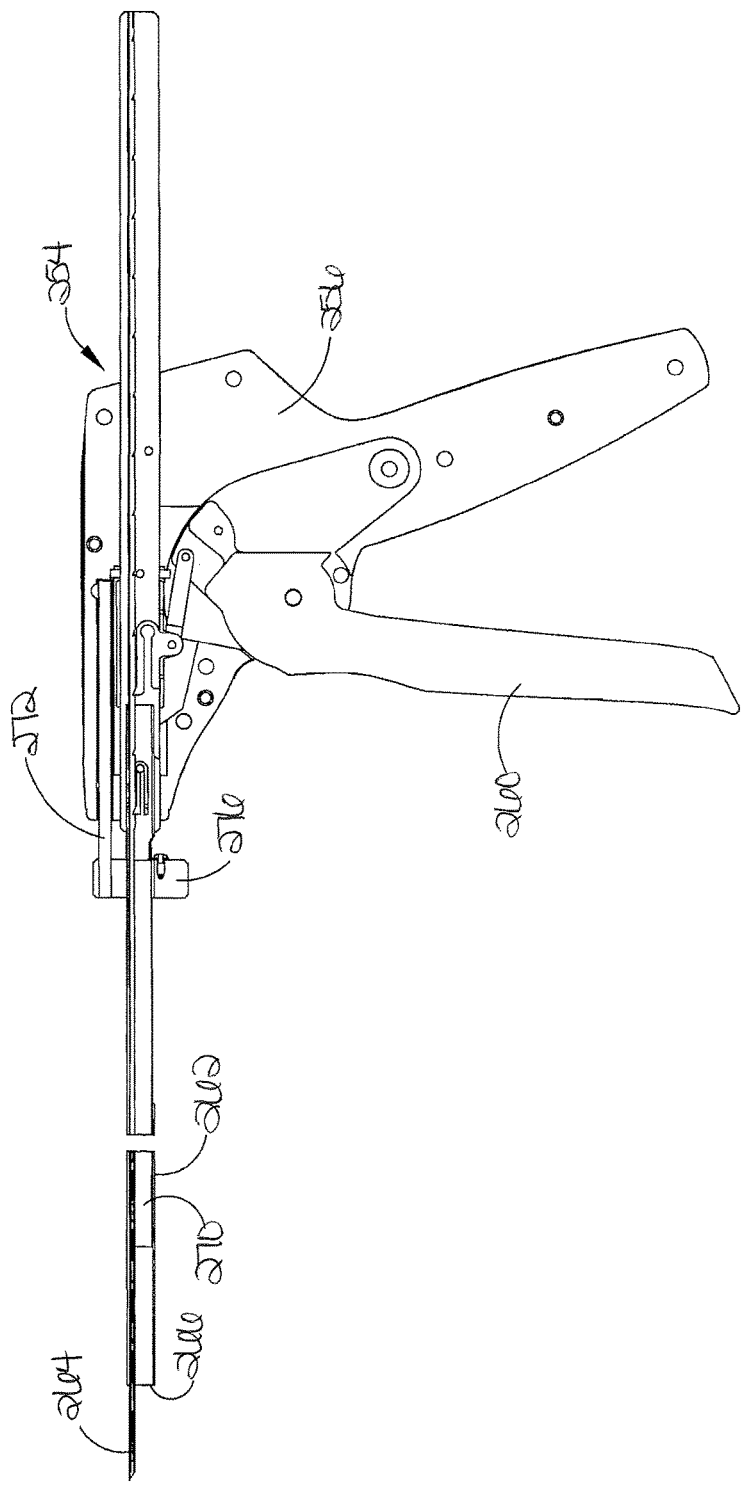
Figure 21A:
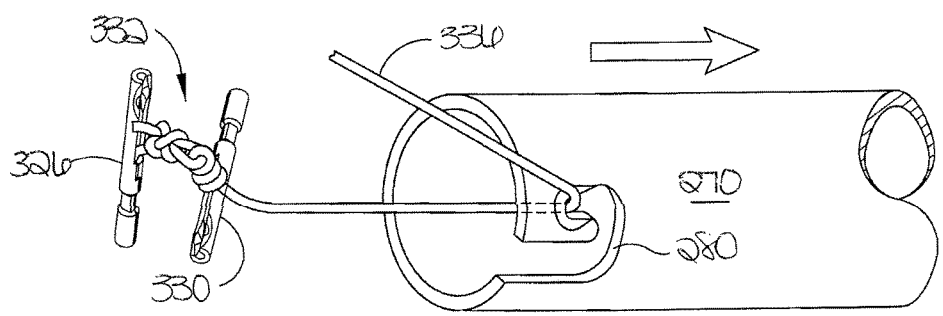
FIGS. 21A and 21B show detailed, perspective views of two separate distal cutting edges of the protective sheath, shown severing a suture.
Figure 21B:
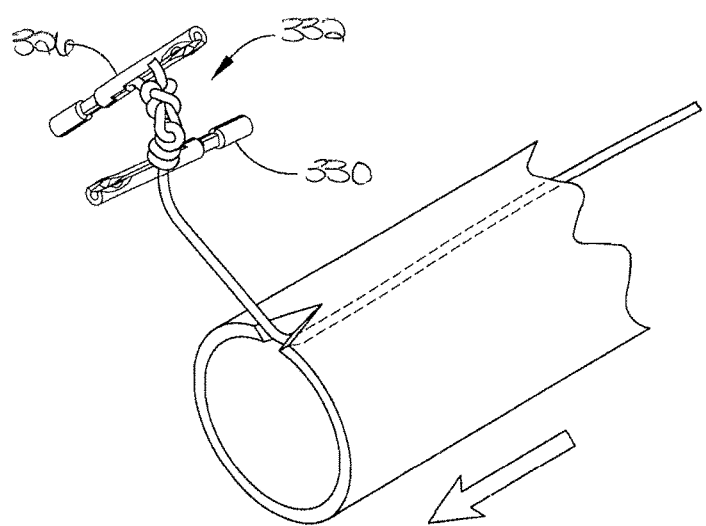

As shown in FIG. 11A, a needle 264 extends distally within the lumen of deployment device housing 262 from handle 254 through the open distal housing tip 266. A retractable, protective sheath 270 extends distally through deployment device housing 262 and over the exposed tip of needle 264. A rod 272 is attached to protective sheath 270 by a ring 276 that extends about the circumference of deployment device housing 262. To retract the sheath, ring 276 is pulled proximally, causing rod 272 to slide within a track 274 in handle 254. As rod 272 slides within track 274, the attached sheath 270 is drawn in a proximal direction away from the needle tip. Rod 272 bottoms out within track 274 when protective sheath 270 is in a fully retracted position, as shown in FIG. 11B. Rod 272 is bent slightly so that the rod must be manually manipulated to slide through track 274. This slight bend in rod 272 prevents the rod from unintentionally retracting into track 274 and leaving the tip of needle 264 exposed. Numerous methods to protect the needle and to shield the needle from accidental sticks may be employed as those skilled in the art will recognize. The deployment device preferably includes a cutting edge for severing suture following T-Tag deployment. In the device shown in FIGS. 10-12, the cutting edge is a hook shaped cutout 280 formed into the distal end of protective sheath 270. Suture extending through deployment device housing 262 can be drawn into the stem of the cutout and trapped and severed at the hook tip. The cutting may be accomplished by shaping the stem of the hook so that it necks down in a sharp 'V' shape, so that when the device pulls the suture into the 'V', it is cut (FIG. 21A). Alternatively, with the suture seated in the stem, a separate sheath may be translated (linear or rotational translation) shearing in a scissors fashion the suture within the stem. Yet another variant is to have a 'V' shaped slit at the distal end of protective sheath 270 with the open end of the 'V' located distal on the device (FIG. 21B). By simply advancing the device so that the suture is forced into the 'V', the suture may be cut. Numerous other methods involving slicing, shearing, and heating the suture causing it to separate may be employed.

Figure 13:
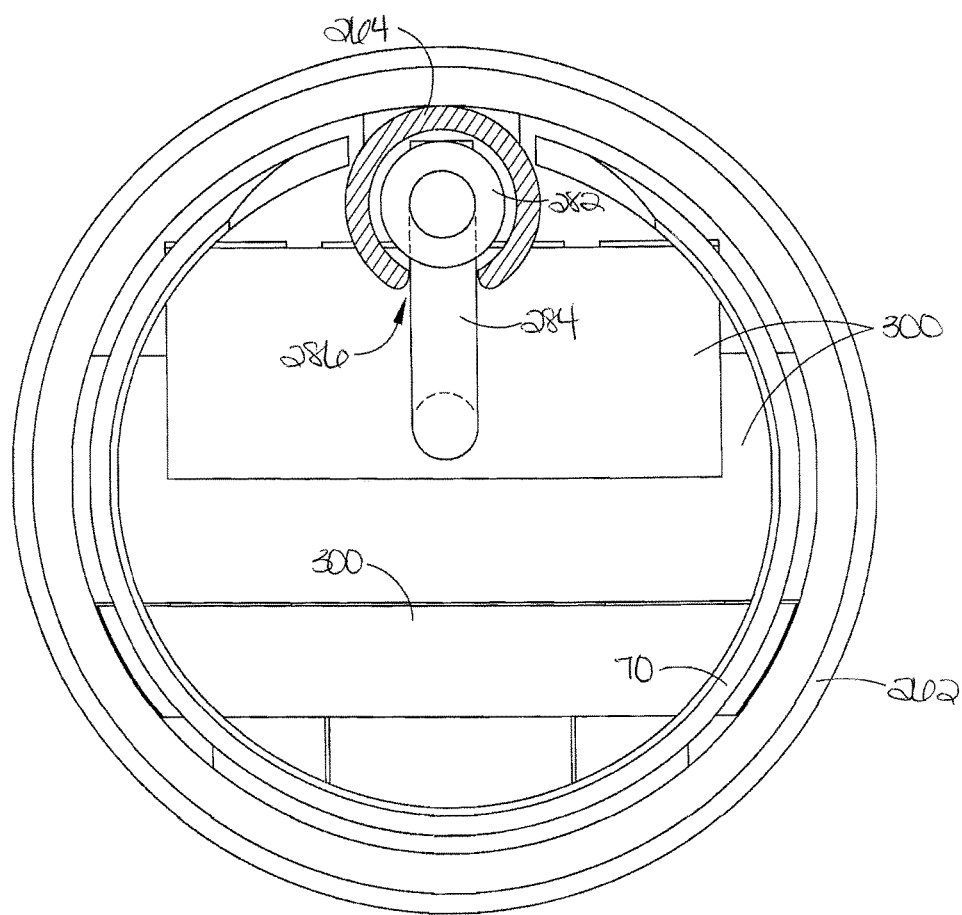
FIG. 13 is a cross-sectional view taken along line 13-13 of FIG. 12, showing the needle shaft and handle portions of the suture anchor deployment device.

Needle 264 includes a slotted lumen that extends proximally from the sharpened tip through deployment device housing 262 for retaining T-Tag anchors. Needle 264 can retain and deploy from one to twenty (or more depending on anchor length) T-Tag anchors, with the particular number of anchors loaded into the needle dependent upon the selected deployment scheme. Multiple T-Tags, indicated by reference numeral 82, can be stacked one against another within the needle lumen. The T-Tag anchors are stacked such that the suture from each tag, identified by reference numeral 284 in FIG. 13, exits the tag in the midsection, perpendicular to the axis of the anchor. The T-Tag anchors and needle slot 286 are aligned so that suture 284 from the T-Tags passes through needle slot 286.

Figure 12:
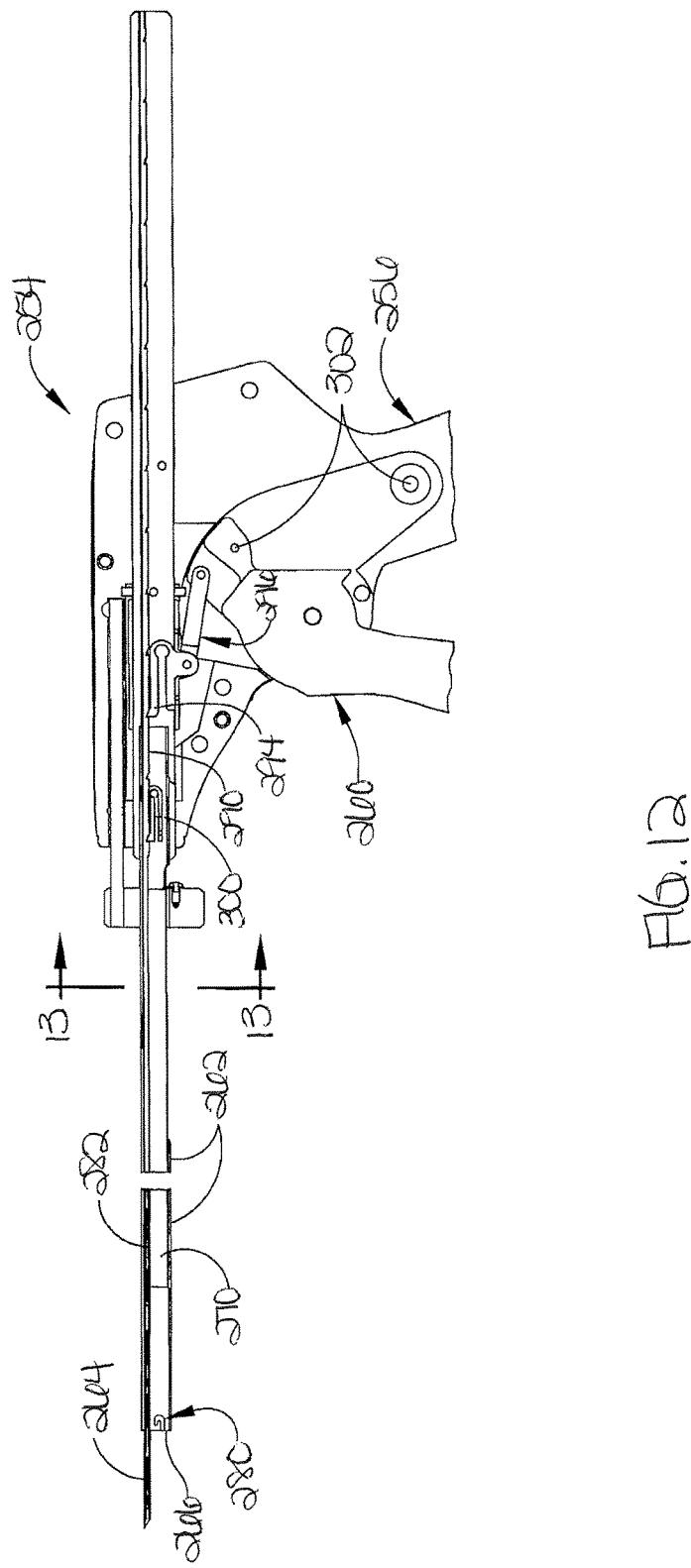
FIG. 12 is a more detailed, cross-sectional view of the suture anchor deployment device of FIG. 10.

As shown in FIG. 12, deployment device 252 includes an actuating mechanism for expelling T-Tag anchors. The actuating mechanism includes a pushrod 290 at the proximal end of the T-Tag anchor stack 282 for advancing and expelling the anchors from the needle. Pushrod 290 includes a plurality of notches which engage a drive pawl 294 for advancing the pushrod distally. Drive pawl 294 is in turn connected through a link 296 to trigger 260. As trigger 260 is pivoted towards pistol grip 256, pushrod 290 is advanced distally (through the link and drive pawl) against the proximal most T-Tag anchor in stack 282. The contact force of pushrod 290 propels anchor stack 282 towards the open distal end of the needle. For each squeeze of trigger 260, a single T-Tag anchor is expelled through the distal tip of the needle and into the adjacent tissue as the stack is advanced distally the length of one T-Tag. As a T-Tag anchor is released, the attached suture exits the deployment device through needle slot 286. An anti backup pawl 300 in handle 254 prevents push rod 290 from moving proximally when trigger 260 is released. An extension spring (not shown) extends between connection points 302 on handle 254 and trigger 260 to provide the necessary force to return the trigger, drive pawl 294 and link 296 to their initial positions when the manual pressure on the trigger is released. The exemplary deployment device shown includes the capability to store and deliver multiple T-Tag anchors during a procedure. Preferably, the deployment device can be reloaded with additional T-Tag anchors when the initial stack is depleted, so that the device may be reused as necessary during the procedure.

FIG. 14 shows a first exemplary T-Tag anchor 310 for deployment from deployment device 252. As shown in the figures, T-Tag anchor 310 comprises an elongated tube 312 having an opening or slot 314 extending approximately one-half the length of the tube. The remaining length of the tube is closed into a cylindrical shape. One end of a length of flexible material, such as suture 316, is inserted into the closed length of tube 312. The end is retained within the tube by crimping the midsection of the cylindrical length, as indicated by 320. The remaining portion of suture 316 protrudes freely out the slot 314. T-Tag anchor 310 may be formed in this manner from flat sheet stock that is rolled into a small diameter tube. A gap may be left in the sheet stock to form slot 314 when the sheet is rolled. T-Tag anchor 310 can also be formed from alternative materials such as, for example, injection molded plastics; or can be manufactured as a solid cylindrical tube with a hole drilled or otherwise formed through the midsection for the suture to protrude through. As shown in FIG. 14, an outwardly extending projection or bulge 322 is preferably formed along the length of T-Tag anchor 310. Bulge 322 creates friction between the inner diameter of needle 224 and the T-Tag anchor 310 when the anchor is held within the deployment device. This friction between the needle and T-Tag anchor prevents the anchor from being unintentionally released from the device. Alternatively, friction between the needle and a single T-Tag anchor may be applied by reducing the needle inner diameter at a distal location so that only the most distal T-Tag anchor is in contact with the high friction area. When loaded into needle 264, T-Tag anchor 310 is positioned so that slot 314 extends adjacent to needle slot 286, so that the free end of suture 316 passes from the anchor through the needle slot. Additional alternative embodiments of T-Tag anchor 310 are described in further detail in commonly owned and co-pending U.S. patent application Ser. No. 11/274,352, filed on Nov. 15, 2005, U.S. patent application Ser. No. 11/274,358, filed on Nov. 15, 2005, and U.S. patent application Ser. No. 11/437,441, filed on May 19, 2006; each of which is hereby incorporated herein by reference in its entirety. Further embodiments of T-Tag anchor 310 are described in commonly owned U.S. Application Publication Number 2006/0025819, the contents of which is hereby incorporated herein by reference in its entirety.

In a first preferred embodiment for forming a tissue plication, a pair of T-Tag anchors are pre-tied together prior to loading the tags into the deployment device. To tie the T-Tag anchors together, a loop or other slidable connecting member 324, such as shown in FIG. 15, is formed in the suture of a first T-Tag anchor. One skilled in the art will clearly recognize that loop 324 may be formed by a variety of different types of knots, such as, for example, a square knot, one or more ½ hitch knots, or a hangman's knot. Alternatively, loop 324 can be formed by drawing suture through an opening 344 in a T-Tag anchor, such as shown in FIG. 18. In this second loop embodiment, a short length of suture 146 extends within an anchor tube 342, and is crimped within the tube at opposite ends, as indicated by 120. Between the crimped ends, the suture is pulled through opening 344 to form loop 324. In an alternative embodiment, an opening can be formed through a first T-Tag anchor so that the anchor itself serves as the sidable member, thereby eliminating the need for a suture loop. In this embodiment, the suture from the second T-Tag anchor is passed through the opening in the first T-Tag anchor to allow the first anchor to slide relative to the second anchor along the length of the suture.

The second T-Tag anchor of the pair is attached at the end of a length of suture. To connect the anchor pair, the suture from the second T-Tag anchor is passed through suture loop 324 of the first T-Tag anchor to allow the first T-Tag anchor to slide relative to the second T-Tag anchor along the length of the suture. After the first T-Tag anchor has been slidingly attached to the suture from the second T-Tag anchor, a one-way slip knot is formed within the suture. The suture knot selves to pull together and lock the T-Tag anchors when the anchors are under load following deployment.

Figure 17A:
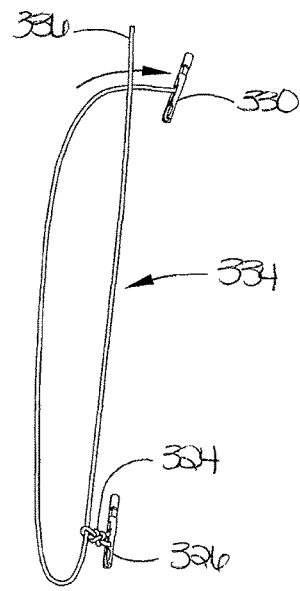
FIGS. 17A-17E show a method of tying the slip knot between the T-Tag anchors.
Figure 17B:
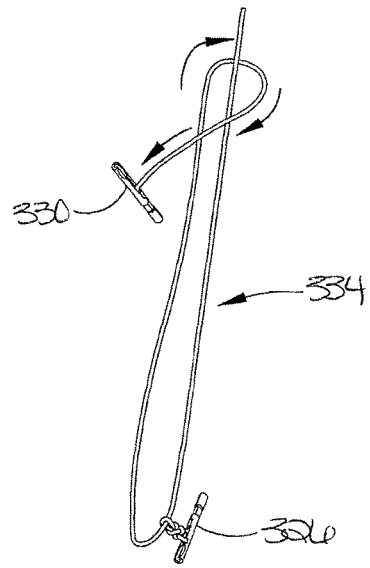
Figure 17C:
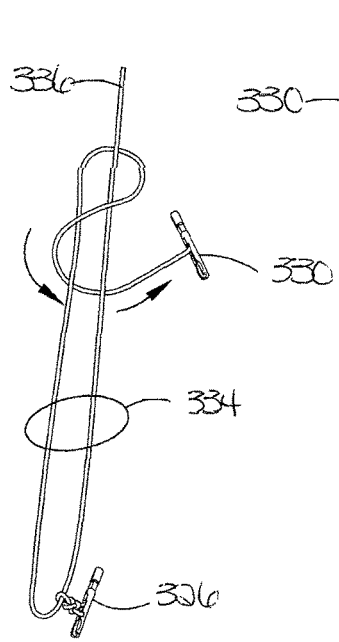
Figure 17D:
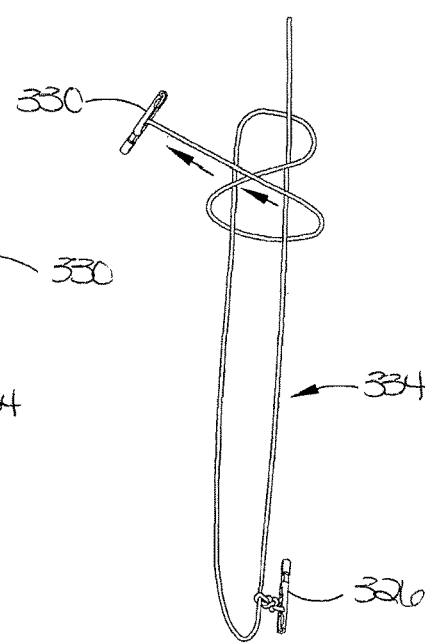
Figure 17E:
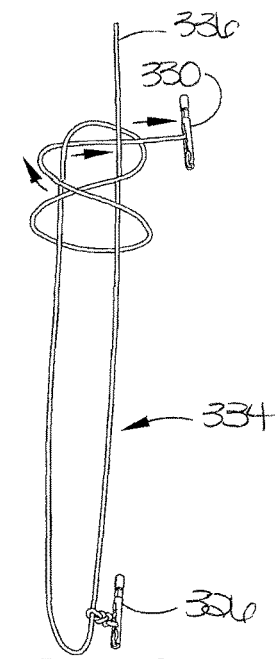

FIG. 16 illustrates an exemplary suture slip knot 332 for drawing together and securing a pair of T-Tag anchors 326, 330. To form slip knot 332, which is one variation of a hangman's noose, the suture length attached to second T-Tag anchor 330 is doubled over, as indicated by reference numeral 334, and the second T-Tag anchor 330 is passed under the suture, as shown in FIG. 17A. Second T-Tag anchor 330 is then encircled back over the doubled suture length 334, as shown in FIG. 17B, and passed back under the doubled suture, as shown in FIG. 17C. To complete the encircling of the doubled suture length 334, second T-Tag 330 is brought over the top of the encircling suture, as shown in FIG. 17D. To complete the slip knot, second T-Tag anchor 330 is brought under the doubled suture length 334 and back over the first encircling pass, as shown in FIG. 17E. When slip knot 332 is fully formed, as shown in FIGS. 16 and 17E, slip knot 332 is tightened setting the distance between slip knot 332 and T-Tag anchor 330, while allowing the doubled suture length 334 to be reduced. Once T-Tag anchors 326, 330 are deployed into tissue, pulling on loose suture end 336 relative to the fixed T-Tag anchors reduces the size of the doubled suture length 334 until it cannot be further reduced because of loop 324. As slip knot 332 is tightened, first and second T-Tag anchors 326, 330 are drawn together. The final distance between first and second T-Tag anchors 326, 330 is defined by the distance from loop 324 to T-Tag anchor 326 and the distance from slip knot 332 to T-Tag anchor 330. The size of loop 324 may also be used to adjust this overall distance. Additionally, where loop 324 is formed by tying a knot in the suture of a first T-Tag anchor 326, slip knot 332 may be pre-tied in the length of suture before the T-tag anchors are attached. Following formation of the slip knot 332, first T-Tag anchor 326 is attached to suture length 334 by tying a knot to form loop 324. Second T-Tag anchor 330 is attached to an end of the suture length by crimping the end within the anchor, and may be done after slip knot 332 is created and tightened. Slip knot 332 is only one example of a suitable knot for fastening together a pair of deployed T-Tag anchors. One skilled in the art will recognize that other slip knots tied such that one anchor is slidably attached to a doubled over portion of the slip knot (such as 334) while the other anchor is secured to a tail or free end of the slip knot remain cinched when forces seeking to loosen the knot are applied only to the anchors in the system. Additionally evident, although not shown, is that a single piece of suture may be used to create slip knot 332 and loop 324. This is accomplished by connecting 336 and 317.

After the suture knot and T-Tag anchor pair are assembled, the anchor pair is preferably loaded into deployment device 252, such that the first "looped" T-Tag anchor 326 deploys initially, followed by the second "attached" T-Tag anchor 330 although the order may be switched. Multiple pairs of the pre-tied T-Tags may be loaded into the deployment device for use during a procedure. For each T-Tag pair, the loose suture end 336 extends from needle slot 286 proximally through the interior of deployment device housing 262. Outside the proximal end of the deployment device housing 262, the loose suture lengths from the multiple pairs of T-Tag anchors are color-coded, labeled, or otherwise distinguished to identify the order of the pairs within the needle stack.

With the pre-tied T-Tag anchor pairs loaded into laparoscopic deployment needle 264, the sheathed tip of the needle is pressed against anterior cavity wall 140 of gastric cavity 132 to probe the outside surface of the cavity, as shown in FIG. 9. The cavity wall indentation can be visualized through endoscope 230 to determine the proper location to insert the needle. Laparoscopic visualization may be used in addition to or in place of the endoscopic view to determine the proper location. After the proper insertion location is determined, protective sheath 270 is drawn proximally along the shaft of needle 264, and the tip of the needle is inserted into anterior cavity wall 140 to reach the interior of gastric cavity 132. Needle 264 is inserted into gastric cavity 132 with sufficient force to prevent the needle from glancing off of the exterior surface of anterior cavity wall 140. Appropriate gastric insufflation pressures ideally provide a sufficiently rigid surface through which the needle may be passed. To prevent the gastric wall from tenting into the cavity interior as needle 264 is inserted (which may allow the posterior gastric wall to be pierced), a grasper may be passed through endoscope 230 and placed against the inside surface of the cavity wall. The grasper provides support on the inside of the cavity wall as the laparoscopic needle is inserted through the wall. Laparoscopic instruments may alternatively be used alone, or in conjunction with endoscopic assistance to allow the needle to safely penetrate a single gastric wall.

When inserting needle 264 through the cavity wall, it is desirable to have as close to normal an angle as possible between the needle tip and the targeted surface of the cavity wall. To facilitate a more direct needle insertion angle, a vacuum assist may be used in conjunction with deployment device 252 to draw the targeted cavity surface against the face of the device just prior to T-Tag anchor deployment. The vacuum assist may be connected to the deployment device, with a vacuum tube extended through the lumen of deployment device housing 262 alongside needle 264. Alternatively, a vacuum tube 352 may be run along the outside of deployment device housing 262 through trocar 250. The tip of vacuum tube 352 and the tip of deployment device 252 simultaneously act upon the same area of tissue, as shown in FIG. 19, to draw the tissue against the face of the deployment device. Following delivery of the T-Tag anchor, the vacuum moves along with the deployment device to additional targeted tissue surfaces.

Figure 20:
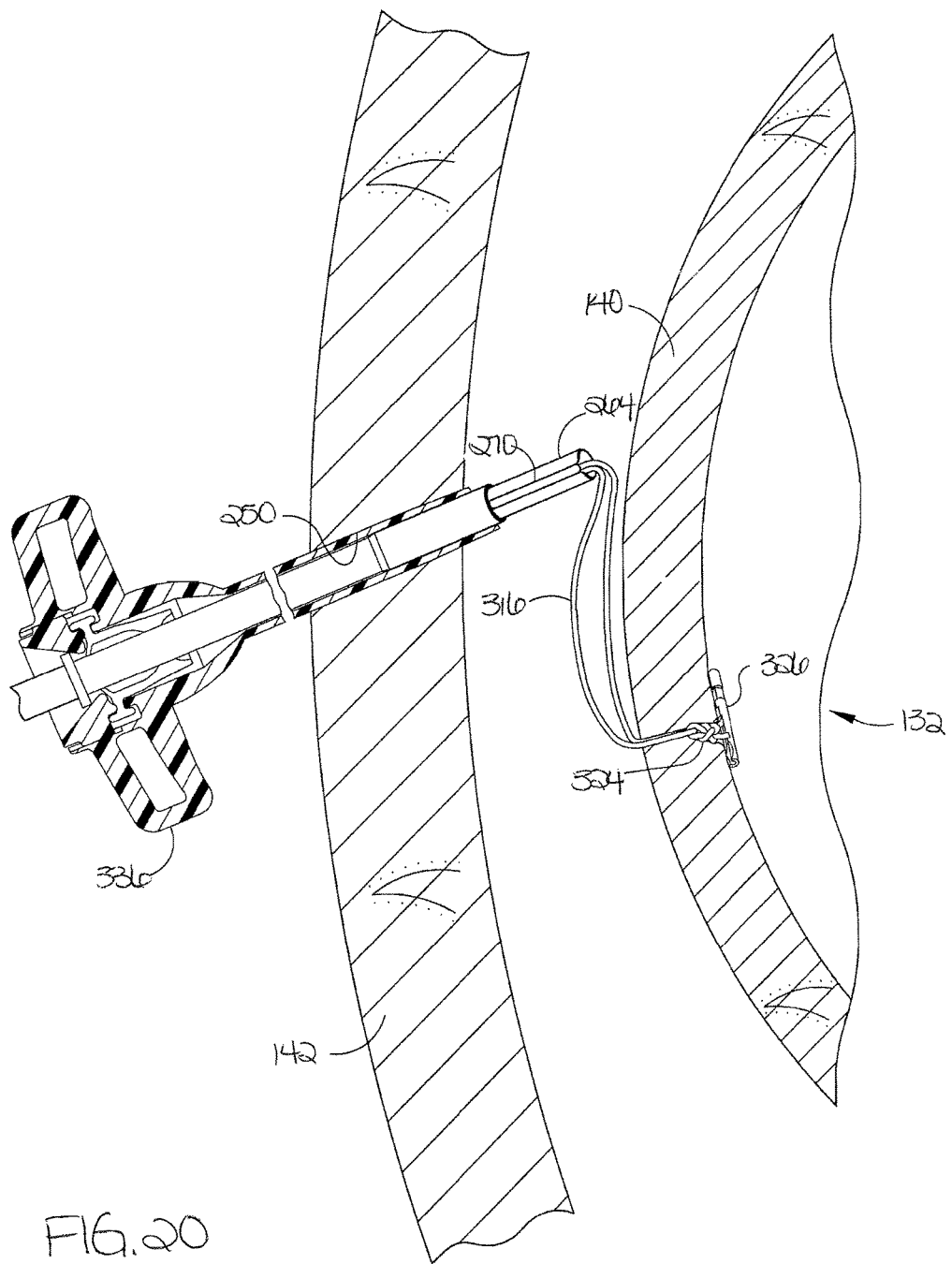
FIG. 20 is a cross-sectional view of an abdominal wall and gastric cavity showing a needle probing the gastric cavity for a second suture anchor location.

After first T-Tag anchor 326 is deployed into gastric cavity 132, either with or without a buttressing device, needle 264 is removed from the cavity. In the preferred case where suture loop 324 tightly surrounds the suture of the doubled over section 334, when needle 264 is removed, a portion of the doubled over section 334 remains in the gastric wall. Alternatively, if suture loop 324 is sufficiently large, as needle 264 is removed, suture loop 324 is drawn from T-Tag anchor 326 back through the cavity wall. After needle 264 is removed from gastric cavity 132, protective sheath 270 is preferably drawn back over the tip of the needle. The anterior wall is again probed with the sheathed needle tip, as shown in FIG. 20, to determine the location for the second T-Tag anchor. To facilitate the anterior wall probing, trocar 250 may be flexed at different angles within abdominal wall 142, as shown in FIG. 20, without removing the trocar from the abdominal wall. Trocar 250 is angled within abdominal wall 142 to enable needle 264 to enter gastric cavity 132 at different locations and in as direct an angle as possible to the exterior cavity surface. Once the proper placement location is determined, needle 264 is once again inserted through anterior cavity wall 140 into gastric cavity 132. With needle 264 inside gastric cavity 132, the second of the pre-tied T-Tag anchors 330 is deployed into the interior of the cavity. Second T-Tag anchor 330 can be deployed with or without a buttressing device.

Figure 22:
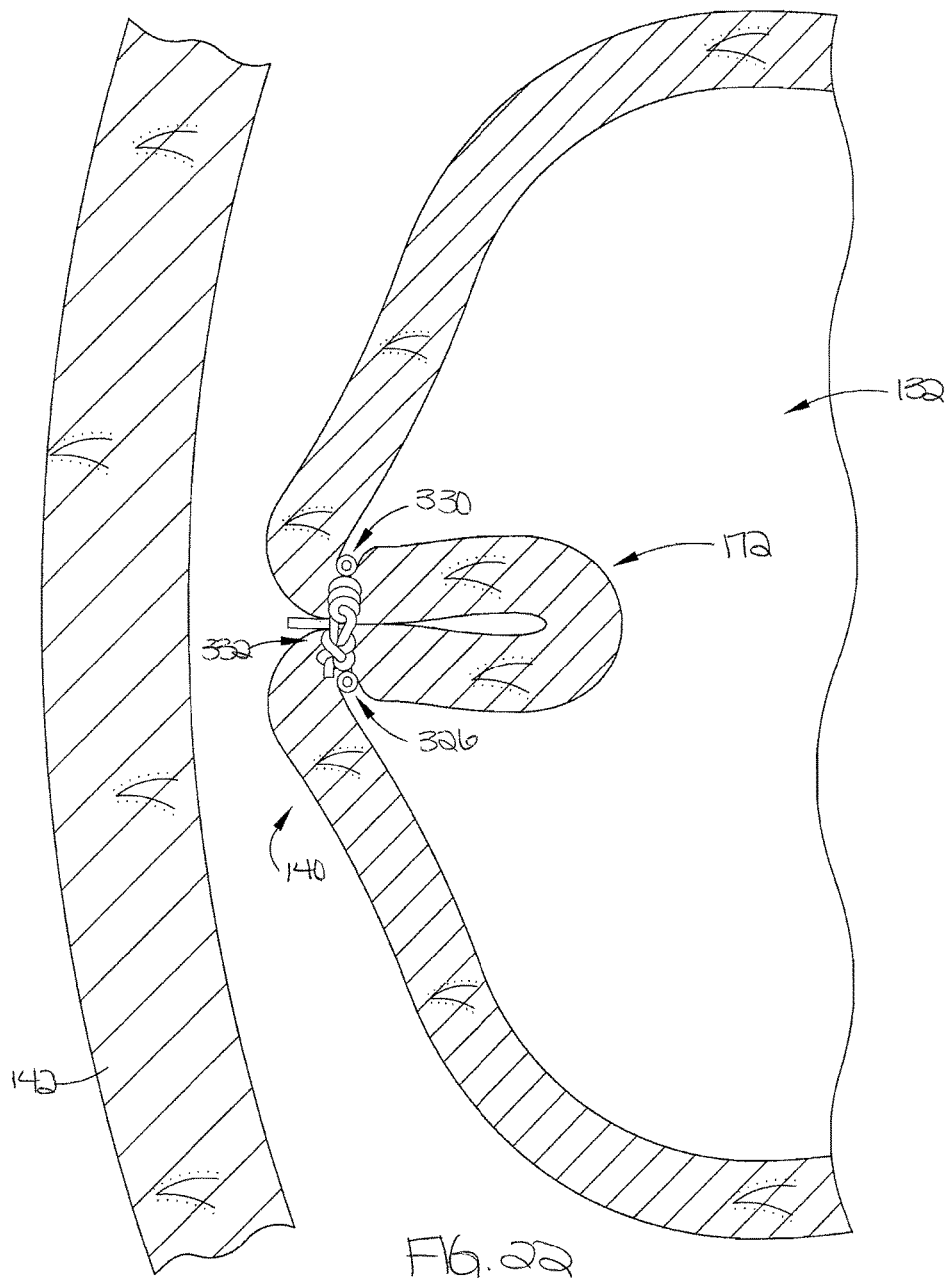
FIG. 22 is a cross-sectional view of an abdominal wall and gastric cavity showing a first embodiment for forming and locking a fold in a gastric cavity wall.

After second T-Tag anchor 330 is deployed, needle 264 is removed from anterior cavity wall 140, drawing the attached suture 316 back through the wall. With the two T-Tag anchors deployed through the cavity wall, tension is applied to loose suture end 336 through deployment device housing 262, to reduce the size of the doubled over suture 334. As this occurs, T-Tag anchors 326, 330 are drawn together, apposing the serosal tissues surrounding each T-Tag anchor. After the T-Tag anchors and connecting suture have been utilized to appose the cavity wall, the loose suture end 336 is maneuvered into the stem of cutout 280 and around the angled cutting edge as shown in FIG. 21A. With tension applied to the proximal, loose end of the suture from outside the deployment device, protective sheath 270 is retracted in the direction indicated by the arrows, to draw the suture taut within cutout 280 and sever the suture. Following severing, loose suture end 336 is withdrawn proximally through trocar 250. FIG. 22 shows gastric cavity 132 with T-Tag anchors 326, 330 cinched and locked together by slip knot 332 to appose the exterior, serosal layer of the gastric cavity wall and form a fold 172. Of course, laparoscopic cutting instruments (such as scissors) may also be used to cut the suture.

As an alternative to using pre-tied T-Tag anchor pairs, T-Tag anchors having separate, attached lengths of suture may be deployed in a spaced relationship through the cavity wall. In this approach, the separate strands of suture from each of the T-Tag anchors extends through the anterior wall and proximally through deployment device housing 262. Tension is applied to the proximal ends of the suture strands outside of the deployment device to appose the cavity wall tissue surrounding the T-Tag anchors. To lock the suture strands and surrounding tissue in a tensioned, apposed state, a knotting element can be applied to the proximal suture ends and advanced through the trocar to the exterior edge of the cavity wall fold. A knotting element is applied by passing the loose, proximal ends of the suture strands through a knotting element applier, such as the knotting element device which is described in commonly owned and co-pending U.S. patent application Ser. No. 11/437,440, filed May 19, 2006, which is hereby incorporated herein by reference in its entirety.

Figure 23:
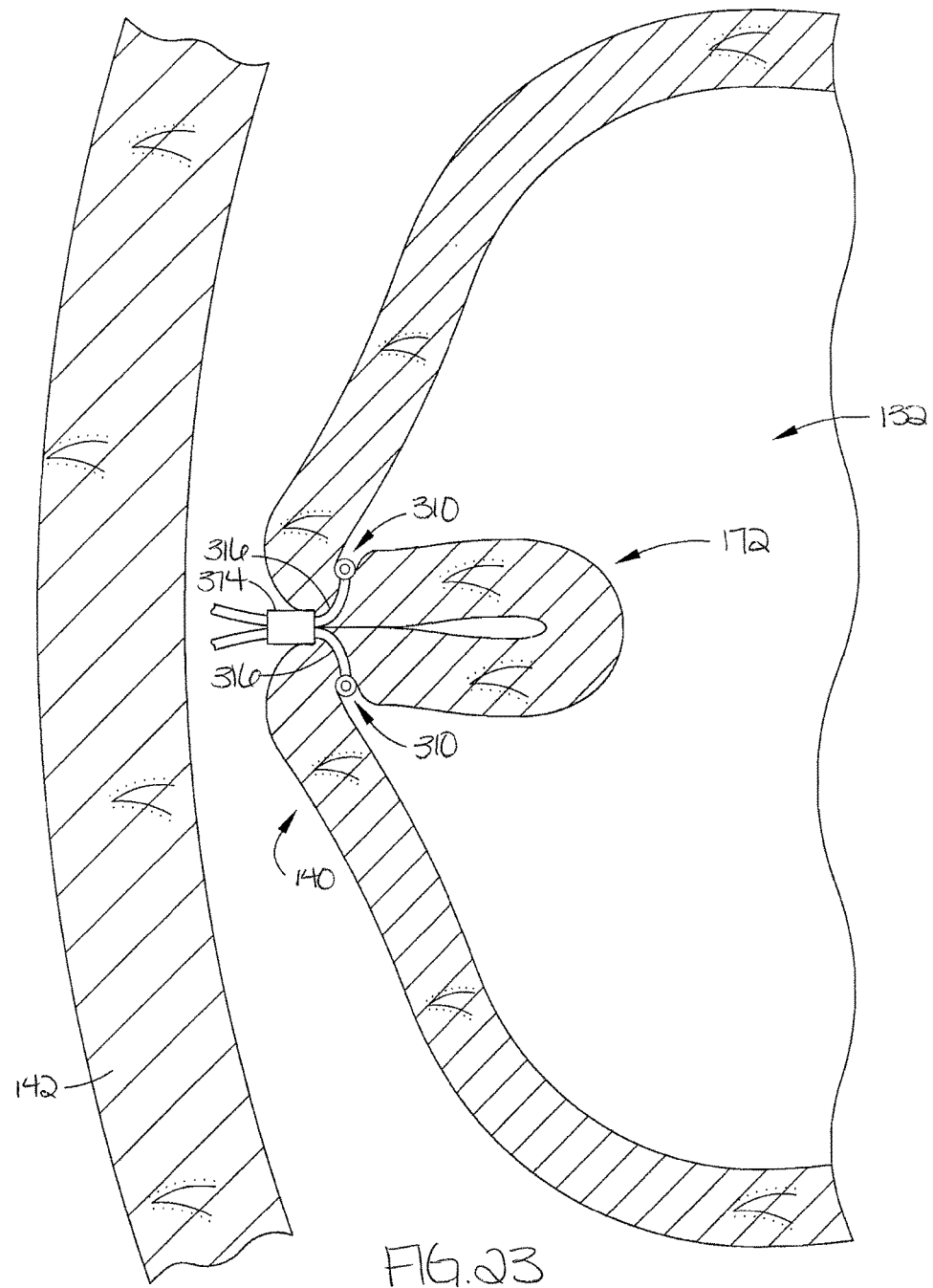
FIG. 23 is a cross-sectional view of an abdominal wall and gastric cavity showing a second embodiment for forming and locking a fold in a gastric cavity wall.

As an alternative for applying a knotting element, the knotting element applier can be loaded or otherwise incorporated into deployment device housing 262 along with a pair of T-Tag anchors, so that the T-Tags and knotting element are all delivered through the deployment device. In this case, the deployment device 252 is loaded with the two T-Tag anchors, and the suture strands from the anchors are extended out needle slot 286. The suture strands are loaded through the knotting element applier, and the applier passed through a slot in deployment device housing 262 and inside protective sheath 270. After the pair of T-Tag anchors is deployed, the knotting element applier is extended distally from the open end of deployment device housing 262. The proximal ends of the suture strands are pulled to appose the tissue surrounding the T-Tag anchors. When satisfactory apposition is achieved, the knotting element device is deployed to fasten the sutures together and cut the sutures. FIG. 23 shows gastric cavity 132 with a pair of T-Tag anchors 310 deployed through the cavity wall. Suture strands 316 from each of the T-Tag anchors are tensioned to pull the surrounding wall tissue into a fold 172. A knotting element 374 is shown applied to the tensioned suture 316 to maintain the cavity wall in the apposed, folded position. Knotting element 374 may also serve as a delivery means for therapeutic agents that provide the patient with an improved outcome.

In addition to separately loading T-Tag anchors and a knotting element applier into a deployment device, the T-Tag anchors and knotting element applier can be assembled together as a cartridge. The cartridge releasably mates with a deployment device so that a single deployment device can fire multiple sets of T-Tag anchors from multiple cartridges. Likewise, a pair of T-Tag anchors and a knotting element applier may be combined together into a single use, disposable deployment device that fires a pair of anchors, cinches suture from the anchors, and then deploys a knotting element to fasten and cut the suture. In another embodiment, a deployment device cartridge may incorporate a Suture Assistant type knot to cinch and fasten suture from T-Tag anchors. As discussed previously, one skilled in the art will recognize variations of knots that can be easily tailored for this application. In this embodiment, the elements of the design for delivering the knot in the Suture Assistant comprise the top half of the device, and the bottom hail of the device contains a pair of T-Tag anchors, a retractable needle, a length of suture connecting the T-Tag anchors, and a hook/gaff for grabbing and tensioning the suture after T-Tag anchor deployment to appose tissue. More description in further detail on the Suture Assistant can be found in U.S. Pat. No. 5,846,254, which is hereby incorporated herein by reference in its entirety.

In addition to applying a knotting element, suture strands 316 can be locked in a tensioned state by tying a knot in the proximal ends of the suture strands. The knot may be tied laparoscopically through trocar 250. Alternatively, the knot may be tied external of the body, and the finished knot passed back through trocar 250 to a point between abdominal wall 142 and anterior cavity wall 140.

Figure 24:
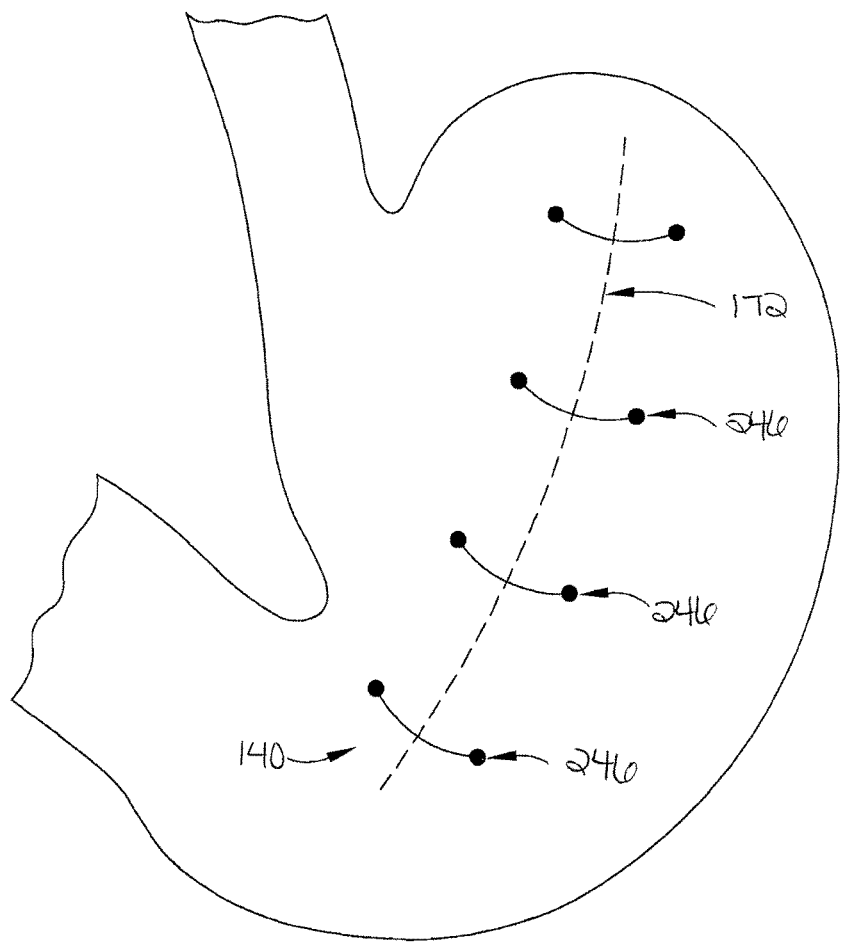
FIG. 24 is a diagrammatic, exterior view of a gastric cavity showing the placement of a first series of suture anchors.

As shown diagrammatically in FIG. 24, one or more additional pairs of tissue anchoring devices 246 may be deployed along the longitudinal length of the cavity wall. The trocar may be flexed within the abdominal wall, or removed and repositioned within the abdominal wall as necessary, in order to reach all of the desired suture anchor locations. Suture material is cinched together between each pair of the devices to extend the length of the cavity wall fold 172. The number of suture anchor pairs used to form a fold will depend upon the desired length for the fold and the desired spacing selected between anchor pairs. Preferably, each of the pairs of suture anchors is evenly spaced apart along the length of the desired fold line. Likewise, within each individual pair the suture anchors are evenly spaced apart across the fold line, so that a uniform tissue fold is formed without distortion or bunching. The proper relative spacing of the tissue anchoring devices can be ascertained through the endoscope. Alternatively, an additional trocar may be inserted into the abdominal wall and used in conjunction with an optical instrument to visually determine the proper locations for the tissue anchoring devices laparoscopically.

Figure 25:
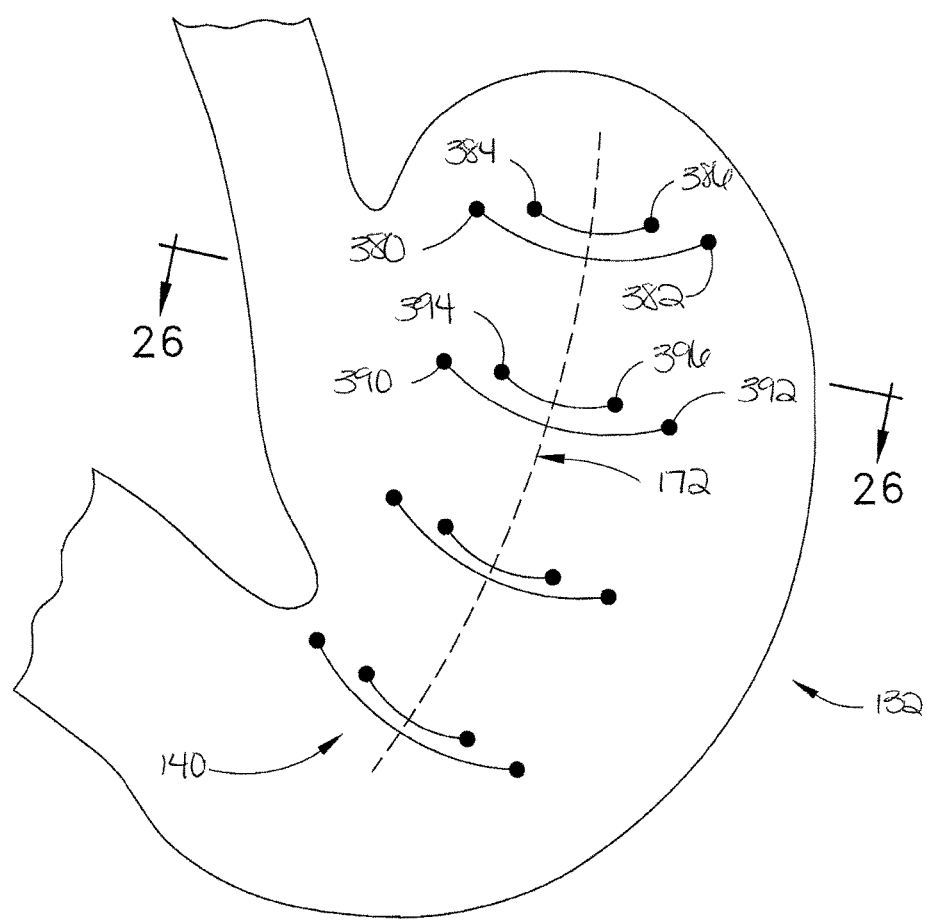
FIG. 25 is a diagrammatic, exterior view of a gastric cavity showing the placement of two series of suture anchors.

After an initial series of T-Tag anchor pairs are deployed into anterior cavity wall 140 and cinched together to form fold 172, a second series of T-Tag anchor pairs is preferably deployed. The second series of T-Tag anchor pairs is deployed to form a second fold about the first fold, increasing the depth of the fold. The depth of fold 172 is determined by the distance between pairs of T-Tag anchors located at the same point along the length of the fold. FIG. 25 shows the exterior surface of anterior cavity wall 140 with a second series of T-Tag anchors deployed to increase the depth of fold 172. In the second series of T-Tag anchors, the anchors are deployed in a spaced relationship from the initial series of T-Tag anchors in a direction away from fold line 172. Accordingly, in the second series of anchoring devices. T-Tag anchors 380, 382 are deployed outside of the initial pair of anchoring devices identified by reference numbers 384, 386. Likewise, second series anchors 390, 392 are deployed outside of the first series anchors identified as 394, 396. Each of the second series of T-Tag anchors are positioned and deployed in the same manner as the initial series of T-Tag anchors. After deployment of each second series T-Tag anchor pair, the anchors are cinched together by tensioning the loose suture end to appose the surrounding cavity wall tissue. The cinched T-Tag anchors are held in place either by a suture knot, such as slip knot 332, by a knotting element, or by other secure means such as the Lapra-Ty® Absorbable Suture Clip, available from Ethicon Endo-Surgery in Cincinnati, Ohio.

Figure 26:
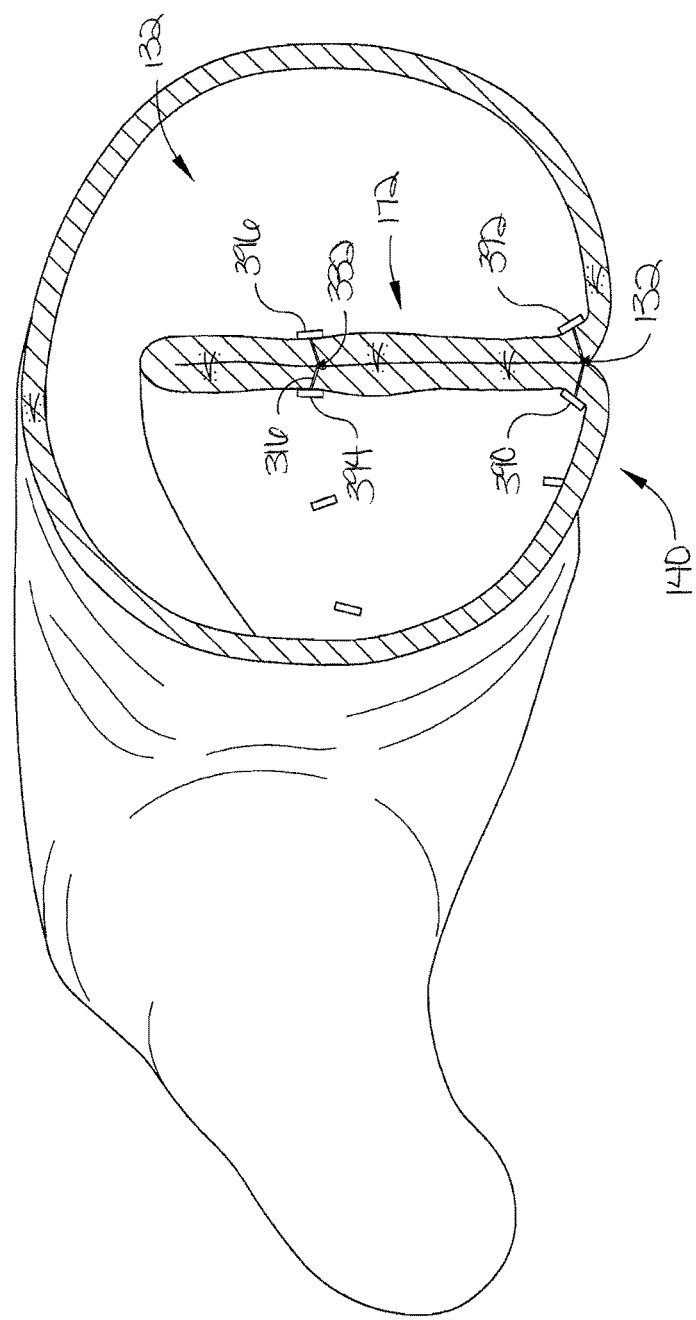
FIG. 26 is a cross-sectional view taken along line 26-26 of FIG. 25, showing the interior of a gastric cavity with a uniform wall fold.

As shown in FIG. 25, the second series of tissue anchoring devices preferably includes the same number of anchoring pairs as the first series, so that a uniform depth fold is created. Each of the pairs of anchoring devices in the second series is aligned longitudinally along the length of the fold with the other pairs of anchoring devices to maintain a uniform line for the fold. FIG. 26 shows two rows of longitudinally spaced T-Tag anchor pairs forming fold 172 in the interior of gastric cavity 132. As shown in this Figure, fold 172 involutes into the interior of the gastric cavity so that the serosal layer of the cavity wall is brought into contact with itself along the center of the fold. As shown in FIG. 26, each pair of T-Tag anchors is pulled together by the attached suture, and the tension in the suture locked in by tightening a slip knot 332. Alternatively, tension may be locked into the suture to hold the cinched tissue together by a knotting element or other type of suture knot. The T-Tag anchoring devices are placed through the cavity wall to maintain the serosal to serosal contact within the fold during healing.

To promote healing along fold 172, the serosa may be affected where the cavity wall portions abut within the fold. The serosa may be affected physically by abrading, or thermally or electrically damaging the targeted areas of the serosa, via the trocar, prior to drawing the tissue areas together. The serosa may also be affected chemically by applying schlerosants, TGF Beta, Keratin or other known surface affecting agents. Traumatizing the serosa in this fashion, either to induce an injury (abrasion), or to enhance healing (Keratin), produces a healing response within the tissue producing a more rapid and potentially more durable formation of an adhesive bond between the contacting serosal surfaces.

Following deployment of the second series of anchoring devices, additional series of anchoring devices may be deployed to further increase the depth of the fold. The additional series of anchoring devices are deployed in a spaced relationship from the previous series of tissue anchoring devices in a direction away from the fold line. Additional series of anchoring devices may be deployed to permanently increase the depth of the fold in which case the spacing between anchor sets is small resulting in a dense line of anchor sets. Alternatively, an additional series of anchoring devices may be deployed to provide reinforcement during the healing process. Following formation of the serosa-to-serosa fold, healing may not occur over the full depth of the fold due to less than full contact between the abutting serosa layers. Accordingly, where deeper healing is desired, a reinforcement series of suture anchors may be deployed to temporarily increase the depth of the fold.

Figure 27A:
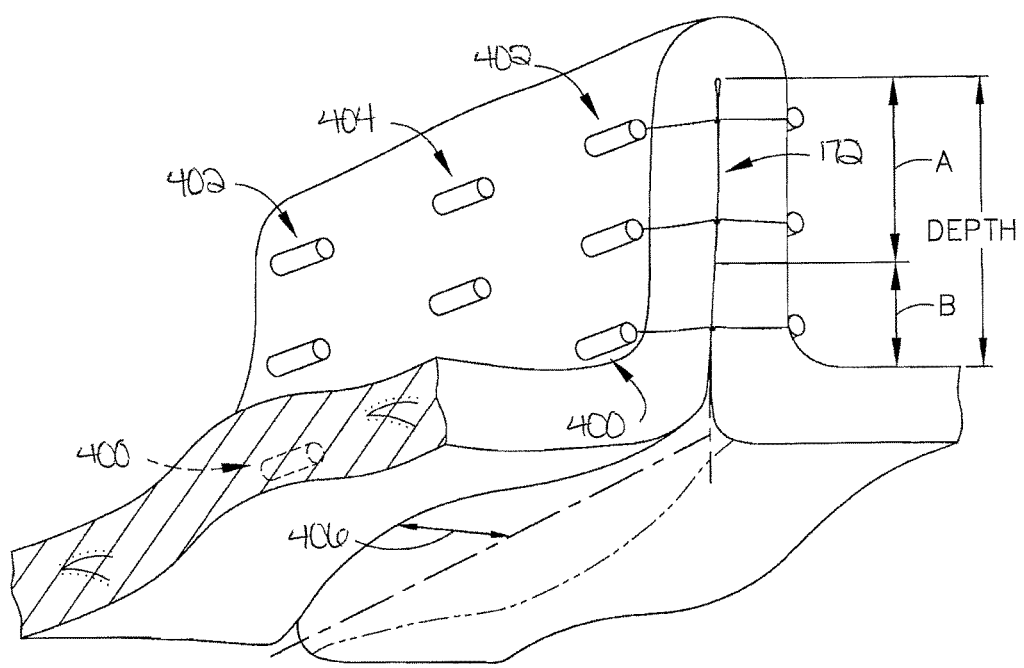
FIGS. 27A and 27B show a perspective and an external view of a portion of a gastric cavity wall fold showing three rows of anchors, the third of which are spaced farther apart than the previous two rows.
Figure 27B:
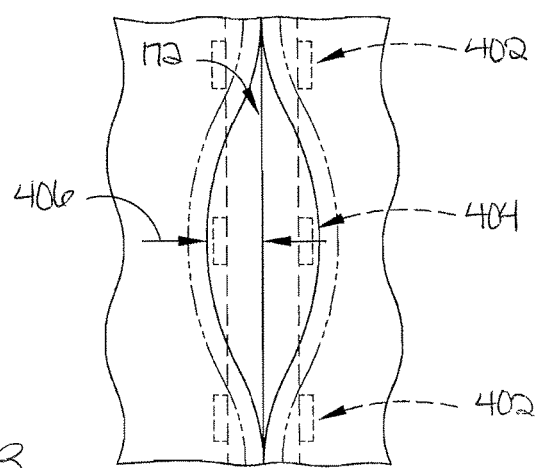

FIG. 27A shows a gastric wall fold section in which a third series of T-Tag anchoring devices is deployed to temporarily increase the fold depth. The third series of anchoring devices, indicated by reference number 400, may be placed at a lower density than the initial series of anchors, yet still promote deeper healing within the fold than would occur without the reinforcement anchors. In FIGS. 27A and 27B, the reinforcement series of anchoring devices 400 is shown with anchors placed only at every other location of the permanent anchors. Thus, three series of suture anchors are deployed at locations 402, while only two series of suture anchors are deployed at location 404. In this example, good serosa-to-serosa healing would occur in zone A, while only marginal healing would occur in zone B, due to the lack of an additional row of suture anchors. Portions of the tissue fold opening may bulge, as indicated by reference numeral 406, due to the reduced number of anchoring devices in the reinforcement series. Bulges 406 coincide with the areas of the fold line that lack a reinforcement anchor. The reinforcement anchors may be designed to fail, be absorbed into the body, or otherwise degrade over time after healing has occurred along the primary depth of the fold. In addition to deploying extra rows of suture anchors through the exterior surface of the cavity, the fold may be reinforced by applying fastening devices including anchors, staples, etc. to the internal side of the cavity wall.

Figure 28:
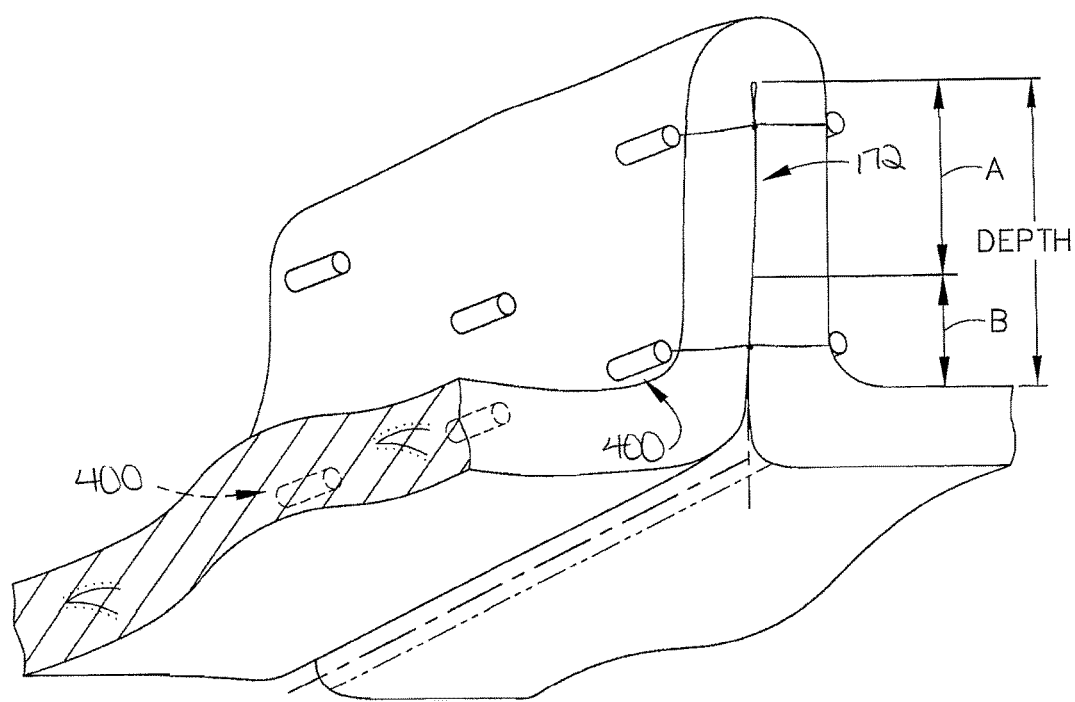
FIG. 28 shows a perspective view of a portion of a gastric cavity wall fold showing three rows of anchors, the third of which is spaced closer together than the previous two rows.
Figure 39:
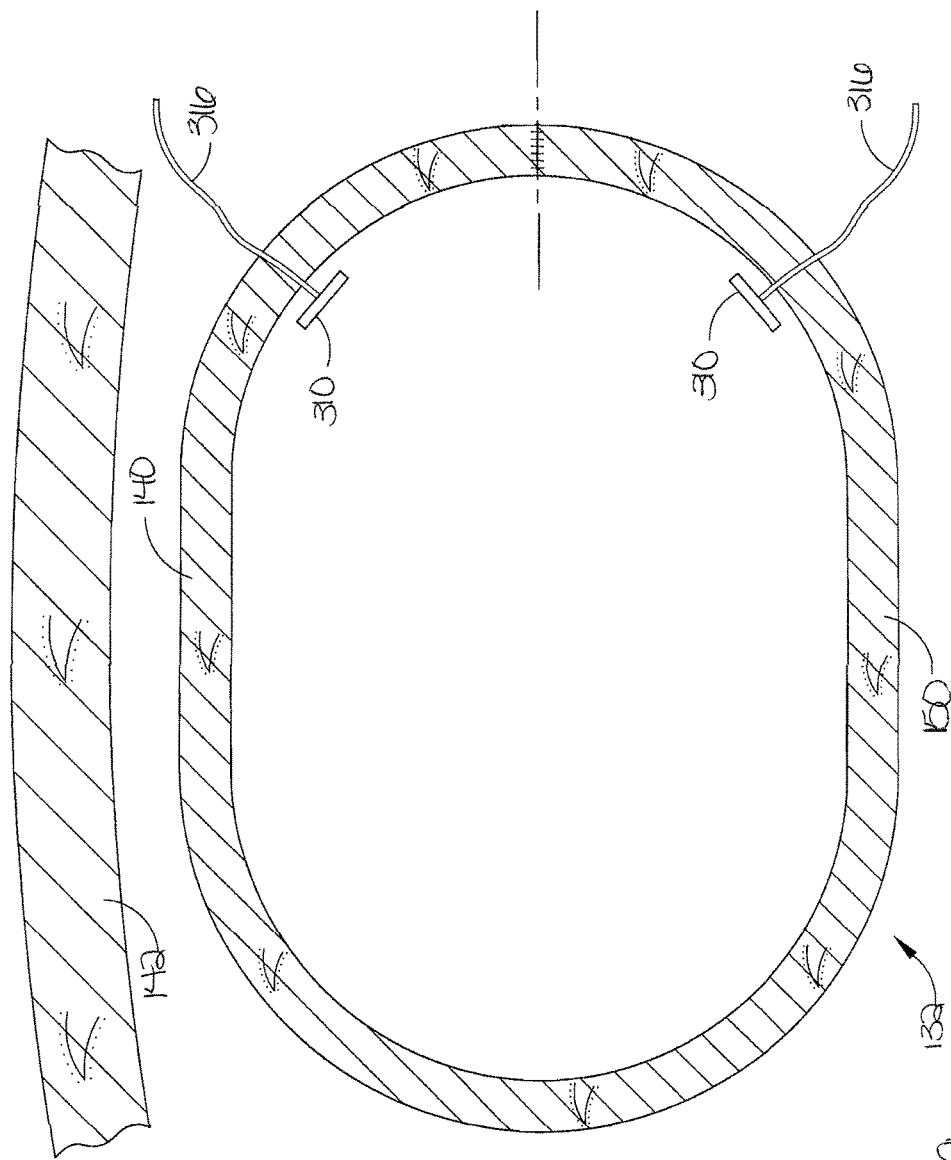
FIGS. 38-43 show several cross-sectional views of different folding patterns.

T-Tag pairs in Zone B are exposed to gastric wall tensions whereas T-Tag pairs in Zone A are likely exposed to much lower stresses. The pattern deployed in FIG. 27A may serve to ensure serosa-to-serosa healing in Zone A, while sacrificing it in Zone B. To increase the likelihood of serosa-to-serosa healing in Zone B, buttress may be selectively used in the region. Yet another alternative to the pattern in FIG. 27A is to have a very dense suture anchor pattern in Zone B, and a less dense pattern in Zone A (see FIG. 28). Numerous patterns can be employed with patterns including numerous combinations of high and low density regions. Buttress may be deployed randomly (if at all), or targeted to high stress areas such as the ends of tows or partially or completely through a load bearing row.

As an alternative to a single, centralized fold in the anterior wall, a large fold may be formed apposing the anterior and posterior walls along the greater curve of the cavity. To form this larger fold, T-Tag anchors 310 are deployed into both anterior wall 140 and posterior wall 150 as shown in FIG. 29. Posterior wall 150 can be accessed through the laparoscope by cutting through the cavity attachment points along the greater curvature. The attachment points can be safely severed provided one of the many redundant blood supplies to the gastric cavity remains intact. After T-Tag anchors 310 are placed in both the anterior and posterior walls, suture attached to the anchors is cinched together and secured by a knot or knotting element to form a deep fold 172 along the greater curve, as shown in FIG. 30.

As an alternative to using T-Tags or other tissue anchoring devices as described above, cavity wall folds may be formed using suture material alone, without an additional anchoring device. In this alternative method, serosa-to-serosa folds are formed by manipulating needles and suture to create suture bites through the cavity wall. Pairs of the suture bites may be cinched together to approximate the tissue into a fold. The Suture bites may be full or partial thickness with the suture material being monofilament, braided, and or absorbable. This suture only method can be accomplished through manual open laparoscopic techniques, or through the use of laparoscopic/endoscopic suturing devices. A number of different commercially available suture applying devices may be utilized to form suture bites in this method. These devices include, but are not limited to, the Ethicon Endo-Surgery Suture Assistant, Auto-Suture (Tyco/US Surgical) Endo-Stitch, Pare Surgical Quick Stitch, Ethicon Endo-Surgery Endoscopic Suturing System, Pare Surgical Flexible Endoscopic Suturing System, and the LSI Solutions Sew-Right suturing system. Following cinching of the suture bites, the cavity wall fold may be secured by laparoscopically tying knots or applying knotting elements as described above.

Figure 31:
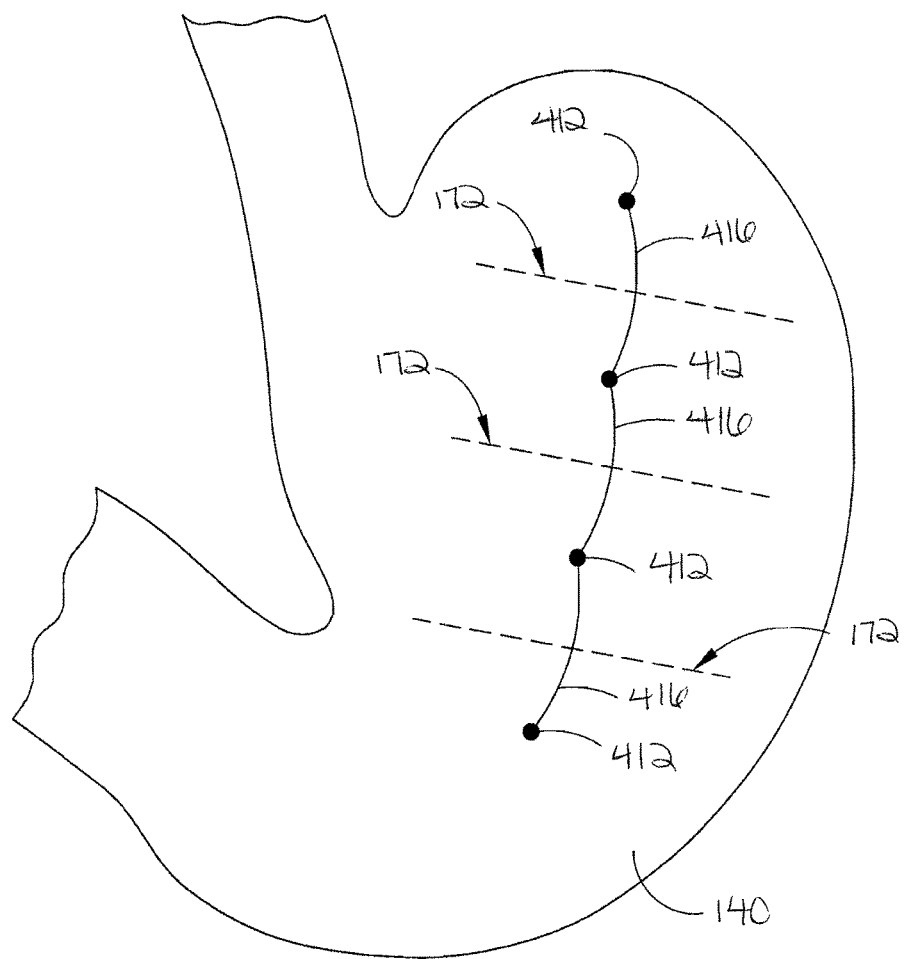
FIG. 31 is an exterior view of a gastric cavity showing a first alternative wall folding embodiment.

FIG. 31 shows an alternative embodiment for forming folds in anterior cavity wall 140. In this embodiment, a plurality of tissue anchoring devices 412 are longitudinally spaced along the length of anterior cavity wall 140. Tissue anchoring devices 412 may be T-Tag anchors, as described above, or any of a variety of other types of tissue fastening devices. Suture material, identified as 416, is cinched and secured between each of the anchoring devices 412 to produce one or more, parallel folds 172 extending across the width of anterior cavity wall 140. In this embodiment, volume reduction is achieved by creating a number of smaller tissue folds, rather than creating a single, long fold. In this example, fold lines do not run proximal to distal, but roughly perpendicular to the midline of the stomach. Of course, any range of angles relative to the midline can be used. One skilled in the art will recognize that orientation as well as length and depth of these one or more folds can be easily varied to achieve the desired effect. As an example and in addition to volume reduction, one or more of these folds may be positioned to create inlet or outlet restrictions.

Figure 32:
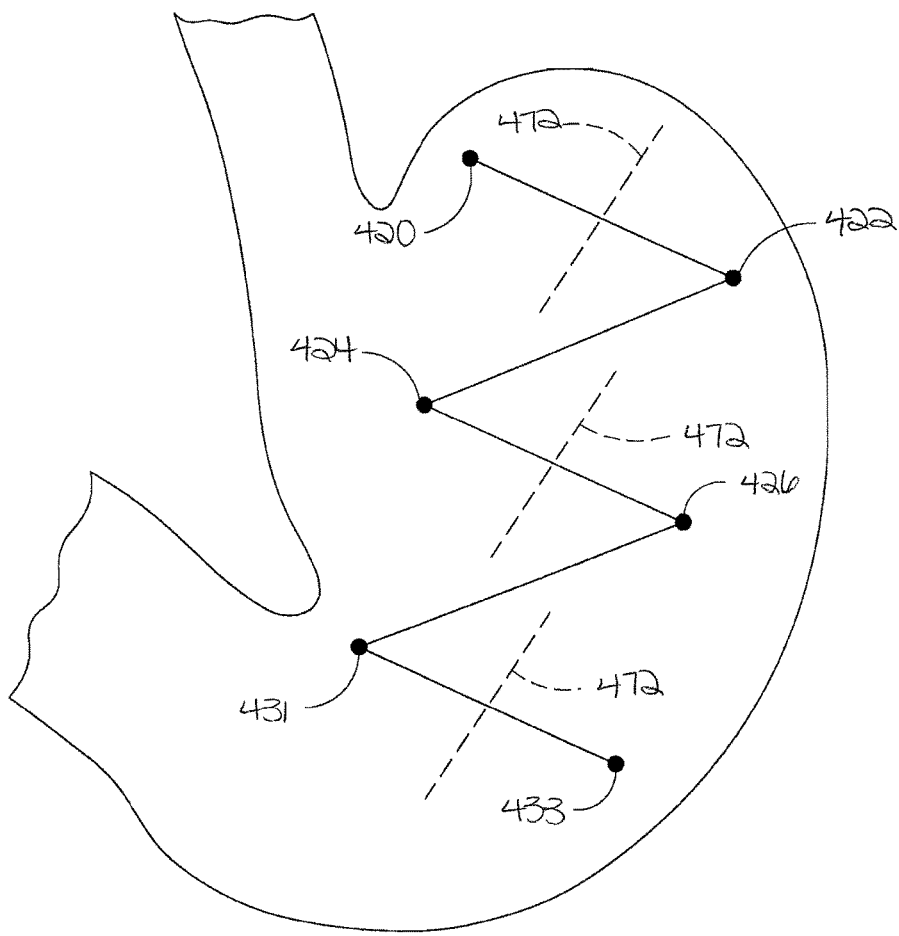
FIG. 32 is an exterior view of a gastric cavity showing a second alternative wall folding embodiment.
Figure 33:
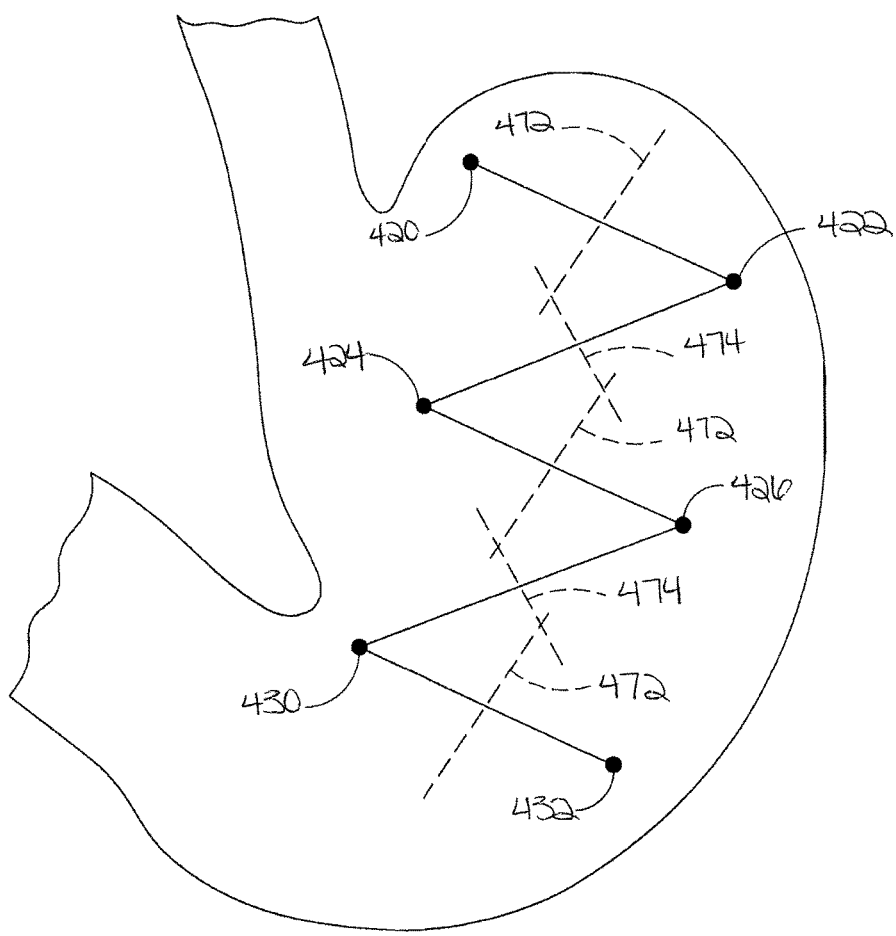
FIG. 33 is an exterior view of a gastric cavity similar to FIG. 32, showing suture tensioned to form an additional set of wall folds.

FIGS. 32 and 33 show a third alternative embodiment for achieving volume reduction through gastric wall folding. In this embodiment, a series of tissue anchoring devices is deployed in anterior cavity wall 140, Individual pairs of suturing anchoring devices are diagonally spaced across the width and length of gastric cavity 132 to form a plurality of folds. In FIG. 32, suture extending between each of the anchoring device pairs 420-422, 424 426, and 431, 433 is tensioned to form parallel-extending, diagonal folds 472. In the embodiment shown in FIG. 33, suture is also cinched between anchoring device pairs 422, 424, and 426, 431 to form an additional set of parallel extending folds 474. Suture extending between the anchoring device pairs may be cinched together and held in place by tightening the pre-tied slip knots between the suture anchor pairs. Where alternative types of suture anchors are utilized, the suture may be cinched and secured by knotting elements, standard suture knots, or the like. In the embodiment shown in FIG. 33, the two different sets of parallel extending fold lines 472, 474 are in different planes, thereby creating a bunching effect within the gastric cavity which reduces the available food volume.

Figure 34:
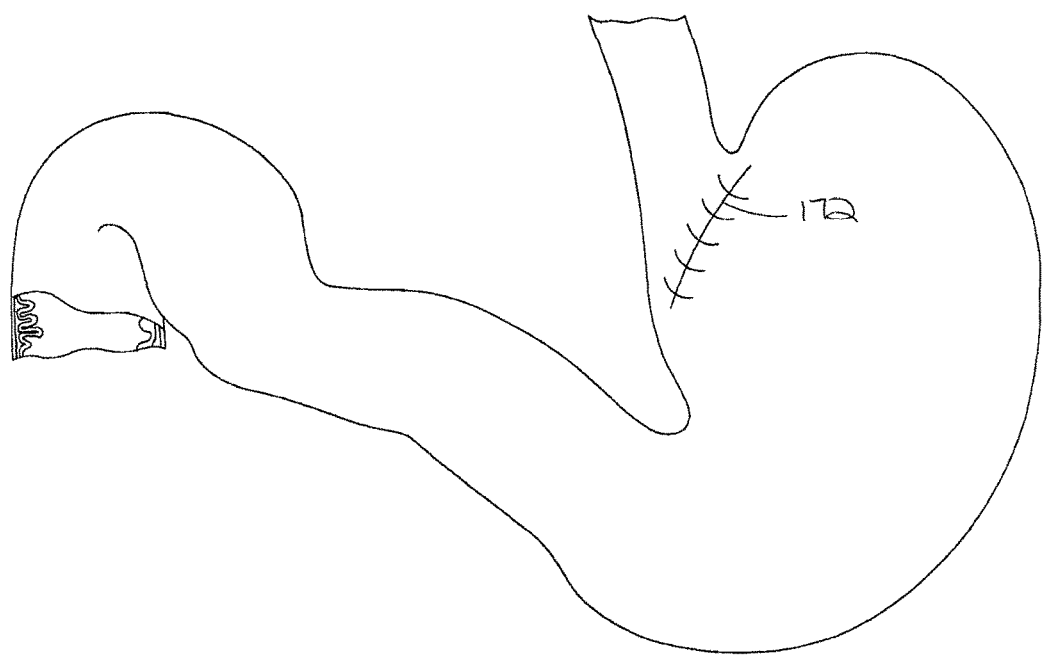
FIG. 34 is an exterior view of a gastric cavity showing a fold placed near the gastroesophageal junction to create a reduced size food pouch or inlet restriction.
Figure 35:
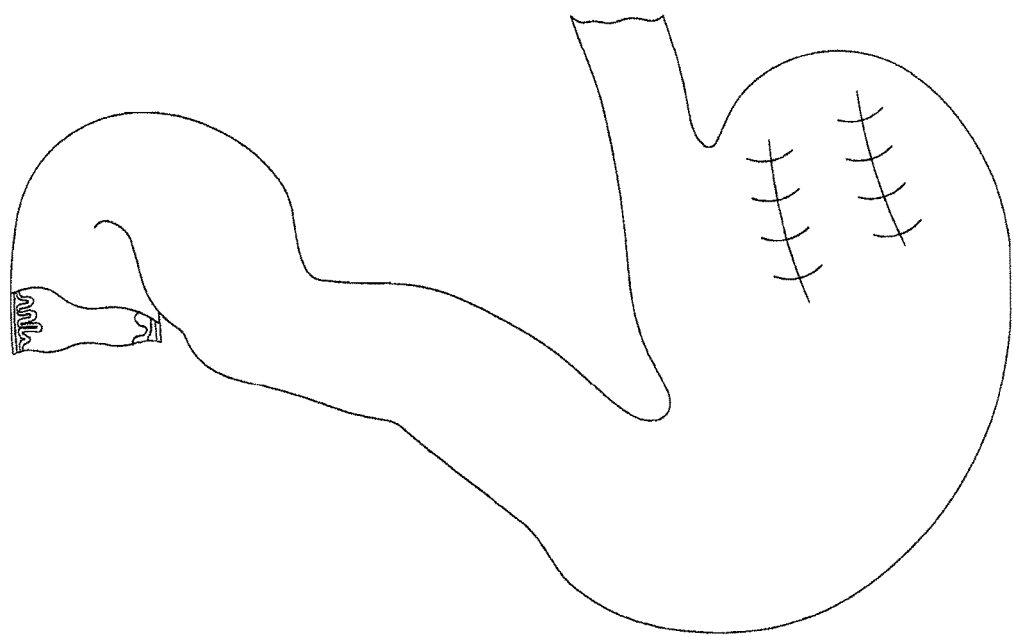
FIG. 35 is an exterior view of a gastric cavity showing folds placed in the fundic region of the cavity reducing gastric capacity and interfering with fundic pressures forcing food into the antral pump.
Figure 36:
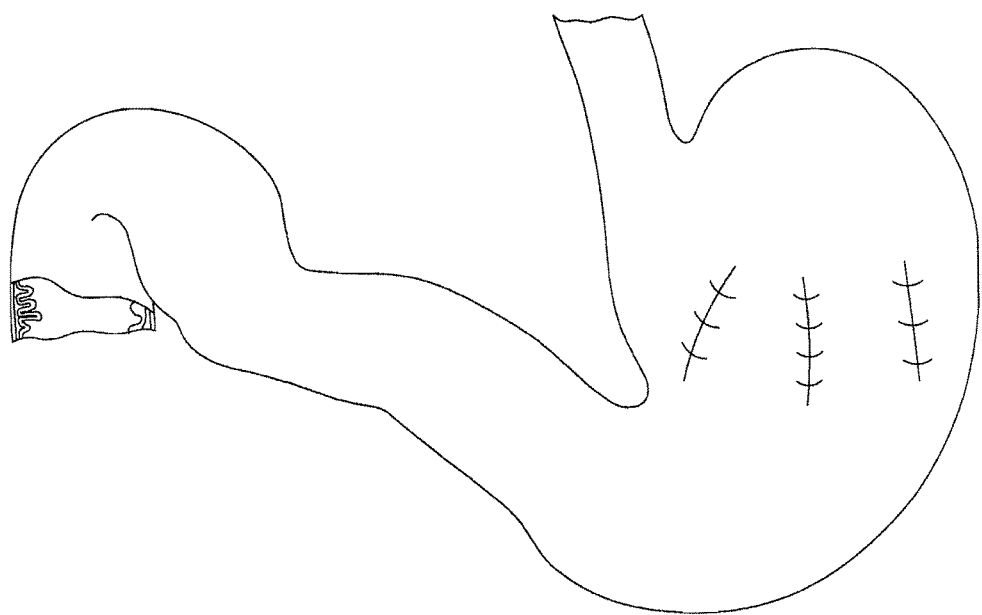
FIG. 36 is an exterior view of a gastric cavity showing folds placed between fundic and distal portions of the cavity reducing volume capacity and altering organ motility.
Figure 37:
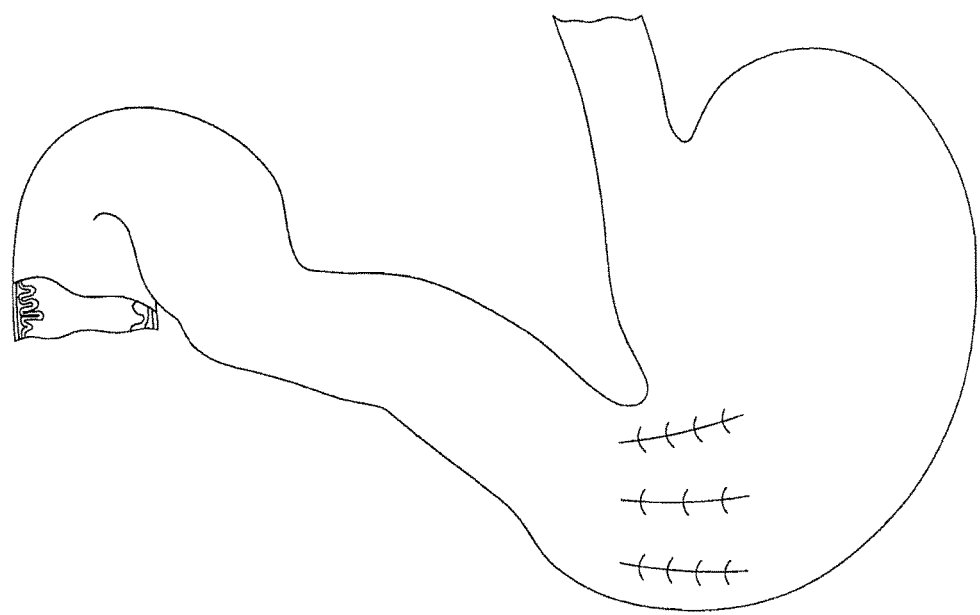
FIG. 37 is an exterior view of a gastric cavity showing a plurality of folds placed in the antrum region of the cavity reducing volume capacity while altering gastric motility and/or introducing an outlet restriction.
Figure 39:
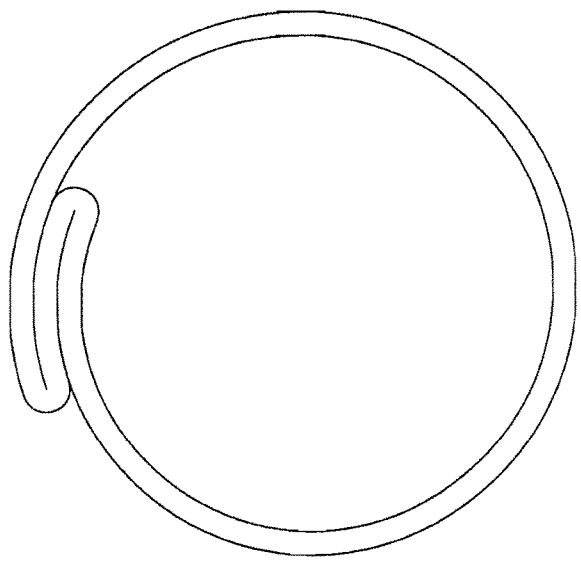
Figure 38:
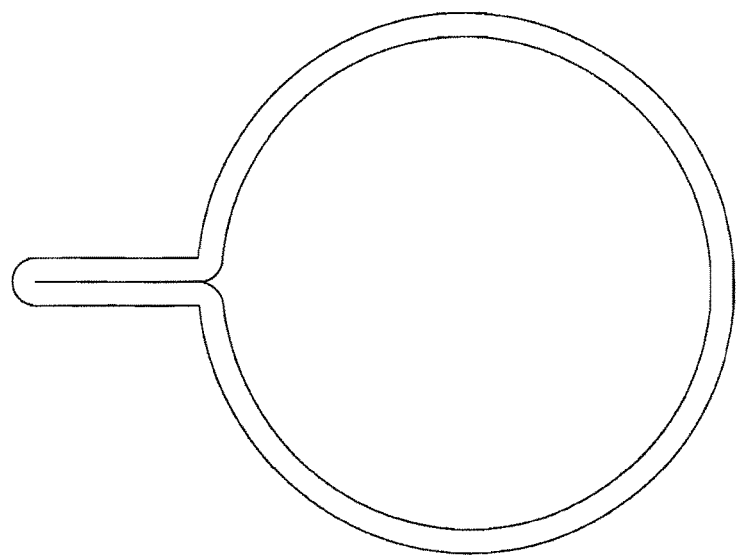
Figure 41:
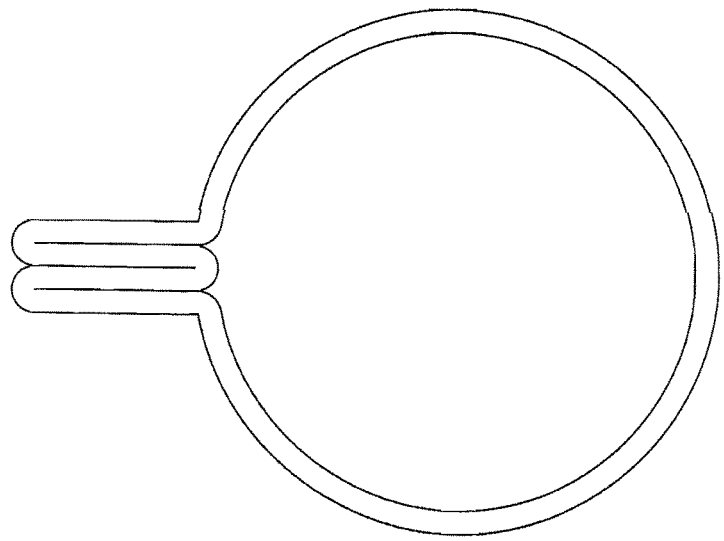
Figure 40:
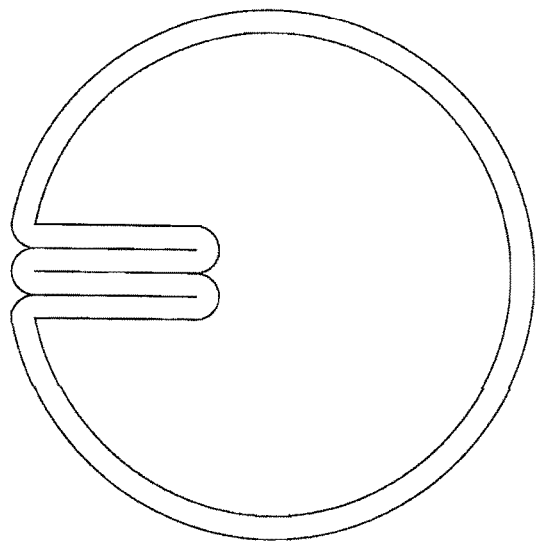
Figure 43:
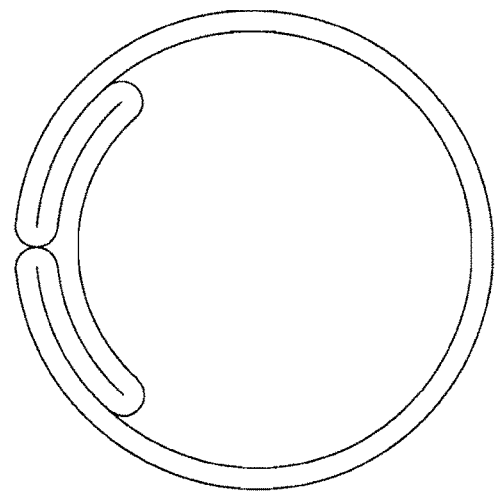
Figure 42:
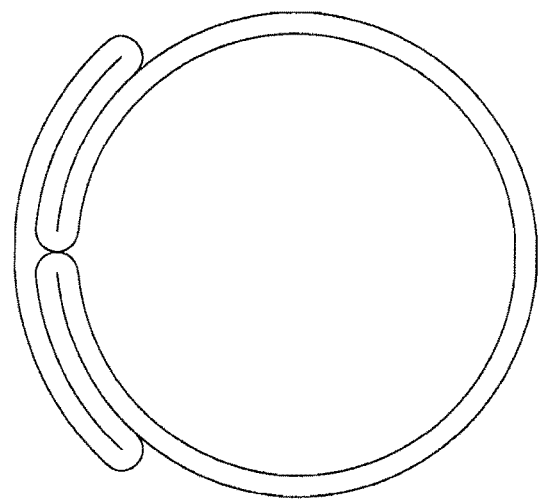

In addition to the embodiments described above, numerous other patterns and locations may be utilized for folding the gastric cavity wall. For example, a fold 172 may be formed in a location between the gastroesophageal junction and the lesser curve of the cavity, as shown in FIG. 34. The fold may be angled towards the lesser curve relative to the gastroesophageal junction to create a reduced-size pouch for food intake and digestion. As discussed above, this type of fold may also create a restriction to food entering the gastric cavity forcing the patient to more thoroughly chew their food. FIG. 35 shows another alternative placement for cavity wall folds. In this example, a pair of folds is placed in the fundic region of the gastric cavity. Locating the folds in the fundic region may lessen distension of the region in response to food intake. The folds may also inhibit the fundic reservoirs ability to produce contractions by either attenuating or baffling the frequency and/or intensity of the contractions, to slow digestion and reduce gastric emptying time. FIGS. 36 and 37 show other alternative placements for cavity wall folds. In these examples, a plurality of folds are placed in the lower region of the gastric cavity. In this location, the folds slow gastric emptying by interfering with the pumping action within the region. In FIG. 36, the folds are placed within the lower region of the cavity extending angularly between the fundic region and a distal portion of the cavity. In FIG. 37, the folds are placed in the antrum region of the cavity. In addition to the above-described embodiments, numerous other fold placements may be utilized without departing from the scope of the invention. The locations, angles and numbers of cavity wall folds may vary depending upon the particular outcome or treatment sought from the procedure. The effects of these folds may include one or more of the following, all of which serve as aids for the patient to lose weight: reduce gastric capacity; restrict passage of food into the gastric cavity; impair breakdown and movement of food within the gastric cavity; restrict passage of food from the gastric cavity; increase production of satiety producing hormones; etc.

One skilled in the art will quickly realize that a wide range of folds shapes and sizes can be used to induce one or more of the effects described above. FIGS. 38-43 show several examples of alternative fold patterns that may also be created with the present invention.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for treating a patient, comprising:
creating at least one incision to gain access to a peritoneal cavity;
performing a gastric volume reduction procedure;
introducing a duodenal sleeve for transporting chyme exiting the stomach to prevent gastric contents in the form of chyme from interacting with at least a portion of a duodenum, the duodenal sleeve including a proximal opening and a distal opening, the step of introducing further includes anchoring the proximal opening to, or distal to, muscle in a pyloric portion of the stomach; and
directing the chyme leaving the stomach inside the duodenal sleeve and bypassing the duodenum such that there is no mixing of chyme with bile until the chyme reaches a jejunum.

2. The method according to claim 1, wherein the duodenal sleeve includes a sleeve and a proximal end having a self-expanding stent.

3. The method according to claim 2, wherein the sleeve is from about one foot to about five feet in length.

4. The method according to claim 1, wherein the step of performing a gastric volume reduction procedure includes forming at least one fold of gastric tissue and securing the fold with a fastener.

5. The method according to claim 4, wherein the fold is on an exterior surface of a gastric cavity apposing exterior, serosal layers of the gastric cavity to form the fold.

6. The method according to claim 5, the fold has serosa-to-serosa contact substantially along its entire length.

7. The method according to claim 4, wherein the fold is formed in an anterior cavity wall.

8. The method according to claim 4, wherein the fastener is a tissue anchoring device.

9. The method according to claim 8, wherein the tissue anchoring device is a T-tag anchor.

10. The method according to claim 4, wherein the step of folding includes physically abrading, or thermally or electrically damaging the gastric tissue.

11. The method according to claim 4, wherein the fold is formed about a greater curvature of a stomach.

12. The method according to claim 4, the fastener is a staple.

13. A method for treating a patient comprising;
creating at least one incision to gain access to a peritoneal cavity;
reducing the capacity of the gastric cavity;
introducing a duodenal sleeve for transporting chyme exiting the stomach to prevent gastric contents in the form of chyme from interacting with at least a portion of a duodenum, the duodenal sleeve including a proximal end and a distal end;
anchoring the proximal end of the duodenal sleeve in the vicinity of a pylorus of the stomach;
extending the distal end of the duodenal sleeve to such that a distal opening at the distal end of the duodenal sleeve extends distally beyond the duodenum; and
directing the chyme leaving the stomach inside the duodenal sleeve and bypassing the duodenum such that there is no mixing of chyme with bile until the chyme reaches a jejunum.

* * * * *